United States Patent
Lange et al.

(10) Patent No.: US 10,687,742 B2
(45) Date of Patent: Jun. 23, 2020

(54) USING INVARIANT FACTORS FOR PULSE OXIMETRY

(71) Applicant: ChroniSense Medical Ltd., Yokneam (IL)

(72) Inventors: Daniel H. Lange, Kfar Vradim (IL); Boris Karelin, Haifa (IL)

(73) Assignee: ChroniSense Medical Ltd., Yokneam (IL)

( * ) Notice: Subject to any disclaimer, the term of this patent is extended or adjusted under 35 U.S.C. 154(b) by 120 days.

(21) Appl. No.: 14/983,118

(22) Filed: Dec. 29, 2015

(65) Prior Publication Data

US 2016/0361004 A1    Dec. 15, 2016

Related U.S. Application Data

(63) Continuation-in-part of application No. 14/738,666, filed on Jun. 12, 2015, and a continuation-in-part of
(Continued)

(51) Int. Cl.
*A61B 5/1455* (2006.01)
*A61B 5/00* (2006.01)

(52) U.S. Cl.
CPC ........ *A61B 5/14552* (2013.01); *A61B 5/6826* (2013.01); *A61B 5/7214* (2013.01)

(58) Field of Classification Search
None
See application file for complete search history.

(56) References Cited

U.S. PATENT DOCUMENTS 3,885,552 A    5/1975   Kennedy
3,898,984 A    8/1975   Mandel et al.
(Continued)

FOREIGN PATENT DOCUMENTS

CN    1335756 A    2/2002
CN    106901747 A   6/2017
(Continued)

OTHER PUBLICATIONS

Arza et al., "Pulse Transit Time and Pulse Width as Potential Measure for estimating Beat-to-Beat Systolic and Diastolic Blood Pressure", Computing in Cardiology 2013, pp. 887-890.
(Continued)

*Primary Examiner* — Etsub D Berhanu
(74) *Attorney, Agent, or Firm* — Carr & Ferrell LLP

(57) ABSTRACT

An example method for performing pulse oximetry can commence with receiving at least three light signals of three different wavelengths reflected from a human tissue. The human tissue includes a pulsatile tissue and a non-pulsatile tissue. Based on the three light signals, values of at least three functions are determined. The three functions are invariant to an oxygen saturation in the pulsatile tissue and depend on location of a sensor operable to detect the three light signals and pressure of the sensor on the human tissue. Based on the values of the three functions, non-pulsatile components are analyzed for intensities of a red light signal and infrared light signal reflected from the human tissue. The non-pulsated components are removed from the intensities to allow correct estimates of a ratio of the absorption coefficients, with the ratio being used to determine the oxygen saturation in the pulsatile tissue.

18 Claims, 15 Drawing Sheets

Related U.S. Application Data application No. 14/738,636, filed on Jun. 12, 2015, and a continuation-in-part of application No. 14/738,711, filed on Jun. 12, 2015.

(56) References Cited

U.S. PATENT DOCUMENTS

| | | |
|---|---|---|
| 4,331,154 A | 5/1982 | Broadwater et al. |
| 4,732,158 A | 3/1988 | Sadeh |
| 4,802,486 A | 2/1989 | Goodman et al. |
| 5,316,008 A | 5/1994 | Suga et al. |
| 5,503,148 A | 4/1996 | Pologe et al. |
| 5,692,505 A | 12/1997 | Fouts |
| 6,047,203 A | 4/2000 | Sackner et al. |
| 6,139,494 A | 10/2000 | Cairnes |
| 6,527,725 B1 | 3/2003 | Inukai et al. |
| 7,184,809 B1 | 2/2007 | Sterling et al. |
| 7,479,111 B2 | 1/2009 | Zhang et al. |
| 7,544,168 B2 | 6/2009 | Nitzan |
| 7,738,935 B1 | 6/2010 | Turcott |
| 8,172,764 B2 | 5/2012 | Gregson et al. |
| 8,602,997 B2 | 12/2013 | Banet et al. |
| 8,866,606 B1 | 10/2014 | Will et al. |
| 10,470,692 B2 | 11/2019 | Lange et al. |
| 2001/0005773 A1 | 6/2001 | Larsen et al. |
| 2001/0029326 A1 | 10/2001 | Diab et al. |
| 2002/0095077 A1 | 7/2002 | Swedlow et al. |
| 2002/0133068 A1 | 9/2002 | Huiku |
| 2003/0009091 A1 | 1/2003 | Edgar, Jr. et al. |
| 2003/0036685 A1 | 2/2003 | Goodman |
| 2003/0065269 A1 | 4/2003 | Vetter et al. |
| 2003/0109776 A1* | 6/2003 | Jacques ............ A61B 5/14551 600/331 |
| 2003/0163033 A1 | 8/2003 | Dekker |
| 2004/0215095 A1 | 10/2004 | Lee et al. |
| 2005/0070775 A1 | 3/2005 | Chin et al. |
| 2005/0215913 A1 | 9/2005 | Lee et al. |
| 2005/0281439 A1 | 12/2005 | Lange |
| 2006/0074322 A1 | 4/2006 | Nitzan |
| 2006/0264767 A1 | 11/2006 | Shennib |
| 2007/0142720 A1 | 6/2007 | Ridder et al. |
| 2007/0191725 A1 | 8/2007 | Nelson |
| 2008/0146954 A1 | 6/2008 | Bojovic et al. |
| 2008/0208069 A1 | 8/2008 | John et al. |
| 2008/0214961 A1 | 9/2008 | Matsumoto et al. |
| 2008/0221419 A1 | 9/2008 | Furman |
| 2008/0255433 A1 | 10/2008 | Prough et al. |
| 2009/0024011 A1 | 1/2009 | Huiku |
| 2009/0163821 A1 | 6/2009 | Sola I Caros et al. |
| 2009/0247848 A1 | 10/2009 | Baker, Jr. |
| 2010/0016694 A1 | 1/2010 | Martin et al. |
| 2010/0179438 A1 | 7/2010 | Heneghan et al. |
| 2010/0192952 A1 | 8/2010 | Melker et al. |
| 2010/0217144 A1 | 8/2010 | Brian |
| 2010/0298656 A1 | 11/2010 | McCombie et al. |
| 2010/0312079 A1 | 12/2010 | Larsen et al. |
| 2010/0324384 A1 | 12/2010 | Moon et al. |
| 2011/0060200 A1 | 3/2011 | Bemreuter |
| 2011/0066051 A1 | 3/2011 | Moon et al. |
| 2011/0077486 A1 | 3/2011 | Watson et al. |
| 2011/0082355 A1 | 4/2011 | Eisen et al. |
| 2011/0201946 A1 | 8/2011 | Turcott |
| 2011/0224564 A1 | 9/2011 | Moon et al. |
| 2011/0257551 A1 | 10/2011 | Banet et al. |
| 2012/0190944 A1 | 7/2012 | Thaveeprungsriporn et al. |
| 2012/0238834 A1 | 9/2012 | Hornick |
| 2013/0231947 A1 | 9/2013 | Shusterman |
| 2013/0296665 A1 | 11/2013 | Kassim et al. |
| 2013/0296666 A1 | 11/2013 | Kumar et al. |
| 2013/0296673 A1 | 11/2013 | Thaveeprungsriporn et al. |
| 2013/0310700 A1 | 11/2013 | Wiard et al. |
| 2013/0338460 A1 | 12/2013 | He et al. |
| 2014/0043164 A1 | 2/2014 | Eschelman et al. |
| 2014/0088449 A1 | 3/2014 | Nearing et al. |
| 2014/0142445 A1 | 5/2014 | Banet et al. |
| 2014/0206948 A1 | 7/2014 | Romem |
| 2014/0275888 A1 | 9/2014 | Wegerich et al. |
| 2014/0278229 A1 | 9/2014 | Hong et al. |
| 2015/0109125 A1 | 4/2015 | Kaib et al. |
| 2015/0148622 A1 | 5/2015 | Moyer et al. |
| 2015/0157220 A1 | 6/2015 | Fish et al. |
| 2015/0157262 A1 | 7/2015 | Schuessler |
| 2015/0196257 A1 | 7/2015 | Yousefi et al. |
| 2015/0272510 A1 | 10/2015 | Chin |
| 2015/0313484 A1 | 11/2015 | Burg et al. |
| 2015/0320328 A1 | 11/2015 | Albert |
| 2015/0342538 A1 | 12/2015 | St. Pierre et al. |
| 2015/0366469 A1 | 12/2015 | Harris et al. |
| 2015/0366518 A1 | 12/2015 | Sampson |
| 2016/0000376 A1 | 1/2016 | Murray et al. |
| 2016/0022220 A1 | 1/2016 | Lee et al. |
| 2016/0089033 A1 | 3/2016 | Saponas et al. |
| 2016/0120434 A1 | 5/2016 | Park et al. |
| 2016/0270668 A1 | 9/2016 | Gil |
| 2016/0270677 A1 | 9/2016 | Lin |
| 2016/0360971 A1 | 12/2016 | Gross et al. |
| 2016/0360974 A1 | 12/2016 | Lange |
| 2016/0360986 A1 | 12/2016 | Lange |
| 2016/0361003 A1 | 12/2016 | Lange et al. |
| 2017/0014037 A1 | 1/2017 | Coppola et al. |
| 2017/0156593 A1 | 6/2017 | Ferber et al. |
| 2017/0202459 A1 | 7/2017 | Gao |
| 2017/0258406 A1 | 9/2017 | Lange |
| 2018/0098705 A1 | 4/2018 | Chaturvedi et al. |
| 2018/0132794 A1 | 5/2018 | Lange |
| 2018/0247713 A1 | 8/2018 | Rothman |
| 2019/0015014 A1 | 1/2019 | Lange |

FOREIGN PATENT DOCUMENTS

| | | |
|---|---|---|
| EP | 2430975 A1 | 3/2012 |
| EP | 3307146 | 4/2018 |
| EP | 3307150 | 4/2018 |
| EP | 3307162 | 4/2018 |
| WO | WO0047108 A1 | 8/2000 |
| WO | WO2001015597 | 3/2001 |
| WO | WO2006048701 A2 | 5/2006 |
| WO | WO2014022906 A1 | 2/2014 |
| WO | WO2015047015 A1 | 4/2015 |
| WO | WO2015197383 A1 | 12/2015 |
| WO | WO2016110804 A1 | 7/2016 |
| WO | WO2016199121 A1 | 12/2016 |
| WO | WO2016199122 A1 | 12/2016 |
| WO | WO2016199123 A1 | 12/2016 |
| WO | WO2016199124 A1 | 12/2016 |
| WO | WO2015070030 A1 | 1/2017 |
| WO | WO2017141131 A1 | 8/2017 |
| WO | WO2017158585 A1 | 9/2017 |
| WO | WO2018025257 A1 | 2/2018 |
| WO | WO2018085563 A1 | 5/2018 |
| WO | WO2019130296 A1 | 7/2019 |
| WO | WO2020053858 A1 | 3/2020 |

OTHER PUBLICATIONS

Ye et al., "Estimation of Systolic and Diastolic Pressure using the Pulse Transit Time", International Journal of Medical, Health, Biomedical, Bioengineering and Pharmaceutical Engineering vol. 4. No. 7, 2010, pp. 303-308.

International Search Report and Written Opinion dated Jul. 11, 2016 in Patent Cooperation Treaty Application No. PCT/IL2016/050511 filed May 15, 2016, pp. 1-19.

International Search Report and Written Opinion dated Aug. 18, 2016 in Patent Cooperation Treaty Application No. PCT/IL2016/050514 filed May 15, 2016, pp. 1-20.

International Search Report and Written Opinion dated Aug. 29, 2016 in Patent Cooperation Treaty Application No. PCT/IL2016/050513 filed May 15, 2016, pp. 1-18.

Patent Cooperation Treaty Application No. PCT/IL2016/050512, "International Search Report" and "Written Opinion of the International Searching Authority," dated Sep. 18, 2016, 9 pages.

"International Search Report" and "Written Opinion of the Inter-

(56) References Cited

OTHER PUBLICATIONS national Searching Authority," Patent Cooperation Treaty Application No. PCT/IL2017/050826, dated Oct. 23, 2017, 9 pages.
"International Search Report" and "Written Opinion of the International Searching Authority," Patent Cooperation Treaty Application No. PCT/IL2017/050242, dated Jun. 13, 2017, 12 pages.
Abtahi, Farhad, "Feasibility of Fetal EEG Recording," Master's Thesis, Department of Signal and System, Chalmers University of Technology, Gothenburg, Sweden, Jan. 1, 2011, 51 pages.
Richardson, Kelly et al., "Electrocardiographic damage scores and cardiovascular mortality," American Heart Journal vol. 149, No. 3, Mar. 1, 2005, pp. 458-463.
"Extended European Search Report," European Patent Application No. 16807014.2, dated Oct. 22, 2018, 8 pages.
"Extended European Search Report," European Patent Application No. 16807015.9, dated Jan. 21, 2019, 10 pages.
Gözde, Ateş et al., "Measuring of Oxygen Saturation Using Pulse Oximeter Based on Fuzzy Logic," Medical Measurements and Applications Proceedings (MEMEA), 2012 IEEE International Symposium, May 18, 2012, pp. 1-6.
"Extended European Search Report," European Patent Application No. 16807013.4, dated Jan. 17, 2019, 7 pages.
"International Search Report" and "Written Opinion of the International Searching Authority," Patent Cooperation Treaty Application No. PCT/IL2018/051384, dated Mar. 14, 2019, 15 pages.
"Office Action," European Patent Application No. 16807013.4, dated Aug. 27, 2019, 6 pages.
"International Search Report" and "Written Opinion of the International Searching Authority," Patent Cooperation Treaty Application No. PCT/IL2019/051018, dated Dec. 17, 2019, 14 pages.
Final Office Action, dated Mar. 22, 2017, U.S. Appl. No. 14/738,636, filed Jun. 12, 2015.
Final Office Action, dated Mar. 29, 2017, U.S. Appl. No. 14/738,666, filed Jun. 12, 2015.
Non-Final Office Action, dated May 17, 2017, U.S. Appl. No. 15/226,881, filed Aug. 2, 2016.
Advisory Action, dated Jun. 16, 2017, U.S. Appl. No. 14/738,636, filed Jun. 12, 2015.
"Extended European Search Report," European Patent Application No. 17836517.7, dated Feb. 25, 2020, 5 pages.
"Office Action," Chinese Patent Application No. 201680042023.6, dated Mar. 20, 2020, 10 pages.

\* cited by examiner

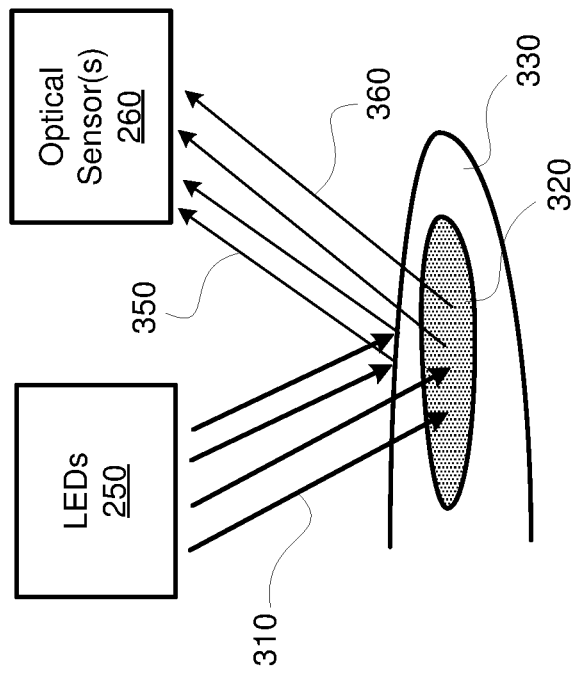
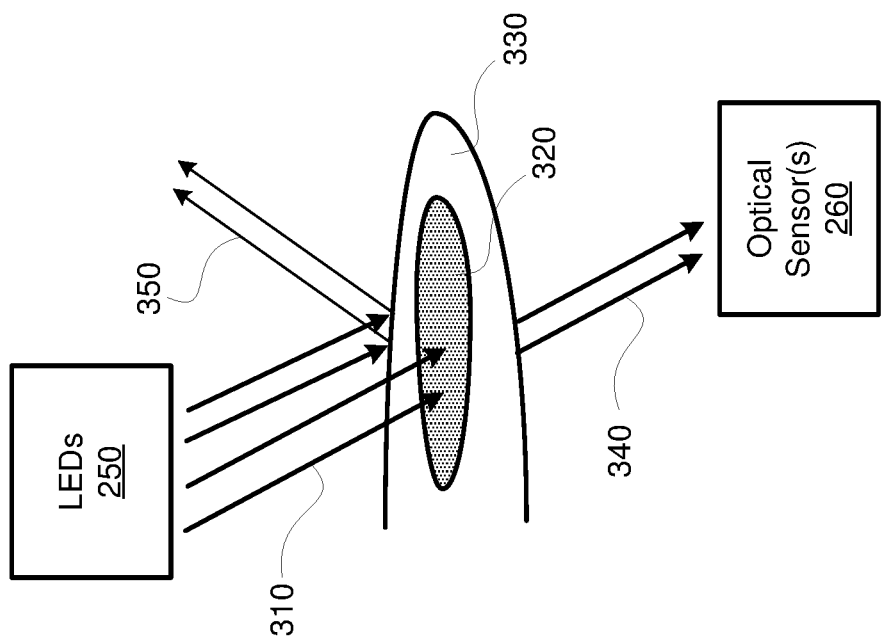
FIG. 3B
FIG. 3A

USING INVARIANT FACTORS FOR PULSE OXIMETRY

CROSS-REFERENCE TO RELATED APPLICATIONS

The present application is a continuation-in-part of U.S. patent application Ser. No. 14/738,666, titled "Monitoring Health Status of People Suffering from Chronic Diseases", filed on Jun. 12, 2015, and is a continuation-in-part of U.S. patent application Ser. No. 14/738,636, titled "Wearable Device Electrocardiogram", filed on Jun. 12, 2015, and is also a continuation-in-part of U.S. patent application Ser. No. 14/738,711, titled "Pulse Oximetry", filed on Jun. 12, 2015. The disclosures of the aforementioned applications are incorporated herein by reference for all purposes.

FIELD

The present application relates to systems and methods for monitoring the health status of people, and more specifically to systems and methods for performing pulse oximetry.

BACKGROUND

It should not be assumed that any of the approaches described in this section qualify as prior art merely by virtue of their inclusion in this section.

Pulse oximetry is a method for estimating blood oxygen saturation by utilizing specialized light sources and optical sensors. Tuned light wavelengths are either transmitted through or reflected from a human tissue and are used to estimate a relative proportion of oxygenated blood. This estimated oxygen saturation, termed $SpO_2$, strongly correlates to arterial blood oxygen saturation. One of the advantages of pulse oximetry over other methods of determining oxygen saturation, such as blood sampling, is that the pulse oximetry is non-invasive, minimally intrusive, generally not painful, portable if it needs to be, and provides for continuous readings.

For a healthy human at normal altitudes, $SpO_2$ is typically 95% or above, with 90% or below indicating hypoxemia, and sustained periods of 80% or below possibly indicating serious medical complications. $SpO_2$ can reflect statuses of individuals suffering from various clinical disorders such as Chronic Obstructive Pulmonary Disease (COPD) or asthma, whether in a stable chronic condition or during an acute phase. Pulse oximetry is also useful in neonatal monitoring, surgical monitoring, or status evaluation when the possibility of oxygen depletion must be considered (pilot monitoring, deep sea diving, and so forth).

Certain clinical conditions can interfere with either the accuracy of pulse oximetry or affect interpretation of results. Diseases which affect peripheral circulation can make the $SpO_2$ an inaccurate estimate of arterial oxygenation. For example, anemia impedes utilization of blood oxygen regardless of the saturation level.

Human activity and behavior can also affect results of the pulse oximetry measurements. Movement of the sensor used in pulse oximetry can interfere with signal acquisition. Temperature changes can affect blood flow to the area being monitored with the sensor. Sweating can affect optical quality. Smoking can increase carbon monoxide which competes with oxygen to bind hemoglobin and can confuse most systems. Contrast dye injections can interfere with blood optical qualities.

Pulse oximetry depends on differences in light absorbance characteristics of oxygenated hemoglobin (oxyhemoglobin) and non-oxygenated hemoglobin (deoxyhemoglobin). The former absorbs light at about 660 nm (in the visible red range) and the latter absorbs light at about 940 nm (infrared). Both light signals, whether reflected or transmitted, fluctuate with the arterial pulse. The resulting signals, photoplethysmograms (PPGs), can indicate volume changes due to blood flow. Pulse oximetry utilizes the intensity change (light signal fluctuation at each heartbeat) for each wavelength to eliminate the confounding optical effects of other tissues (which remain constant). $SpO_2$ can be estimated using the Beer-Lambert Law, which relates to light absorbance due to the concentration of a substance in media, and empirically-derived reference curves from blood samples of hypoxic volunteers, based on the ratio of these changes in each wavelength (delta 660 nm/delta 940 nm), although other complex factors are often included in the calculations.

Typically, the light sources are light-emitting diodes (LEDs) optimized for output at each of the target wavelengths. A single optical sensor (often a photodiode) may be used for both. Each LED can be activated separately, and accompanied by a "dark" period where neither is on (to obtain ambient light levels). The sensor records light transmitted or reflected for each LED. The obtained signals can be processed in real time or offline.

The sensors can be utilized in either a transmission or a reflectance mode. In the transmission mode, the sensor is typically attached or clipped to a translucent body part (finger, toe, earlobe, and so forth). The LED light sources can be positioned on one side of a body part and the sensor can be positioned on the directly opposite side. The light passes through the entirety of the body part, from one side to the other, and is thus modulated by the pulsating arterial blood flow. In the reflectance mode, the light source and the sensor are on the same side of the body part (e.g. a forehead, finger, and wrist), and the light is reflected from the skin and the underlying near-surface tissues back to the sensor.

Despite the conceptually different optical paths in the reflectance pulse oximetry and transmission pulse oximetry, conventional transmission type signal processing can be used for determining of oxygen saturation. However, the sensor part may need to be adapted to enhance the reflectance signal and the usage of a transmission model for reflectance analysis can result in unstable and erroneous $SpO_2$ estimates.

Continued monitoring of chronic outpatients can be greatly enhanced by accurate $SpO_2$ measurements. A reflectance device can be worn on body parts such as a wrist or an ankle and would impose minimal burden on normal activities. Thus, developing reliable reflectance oximetry devices based on a specific light reflectance model holds great promise for outpatients suffering from chronic diseases.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to one aspect of the present disclosure, a system for performing pulse oximetry is provided. An example method includes receiving at least three light signals reflected from a human tissue. The human tissue includes a pulsatile tissue and a non-pulsatile tissue. The three light signals are associated with at least three different wavelengths. The method allows determining, based on the three light signals, values of at least three functions. The three functions are invariant to oxygen saturation in the pulsatile tissue. The method includes determining, based on the values of the three functions, a first non-pulsatile component and a second non-pulsatile component.

The method includes removing the first non-pulsatile component from an intensity of a red light signal reflected from the human tissue to estimate a first corrected intensity. The method includes removing the second non-pulsatile component from an intensity of an infrared light signal reflected from the human tissue to estimate a second corrected intensity. The method also includes calculating, based on the first corrected intensity and the second corrected intensity, a ratio of a red light absorption coefficient and an infrared light absorption coefficient. The method allows determining, based at least partially on the ratio of the first absorption coefficient and the second absorption coefficient, at least the oxygen saturation in the pulsatile tissue. The pulsatile tissue can include an artery, and the non-pulsatile tissue can include skin. The human tissue can include one of the following: a fingertip, a wrist, an ankle, a neck, a chest, and an earlobe.

In some embodiments, the three light signals include a red light signal, an infrared light signal, and an isosbestic light signal. In some embodiments, the isosbestic wavelength signal includes one of a near infrared light signal and a green light signal.

In some embodiments, values of the three functions are maximums of intensities of the three light signals. In certain embodiments, the first non-pulsatile component and the second non-pulsatile component are determined based on an empirically-derived lookup table.

In some embodiments, the three functions depend on physical conditions. The physical conditions can include at least a location of a sensor on the human tissue and a pressure exerted by the sensor on the human tissue. The sensor is operable to detect the three light signals.

In some embodiments, the method includes mapping the physical conditions to the values of the at least three functions. The following operations can be repeatedly performed. The physical conditions are changed by changing a location of the sensor and pressure of the sensor on the human tissue. The three light signals reflected from human tissue are detected for a predetermined period of time. The values of the three functions are determined based on the three light signals.

In some embodiments, the method includes acquiring a reference PPG waveform. The method allows determining first similarity measures between a pre-determined number of waveforms of the red light signal and the reference PPG waveform. The method includes determining second similarity measures between the pre-determined number of waveforms of the infrared light signal and the reference PPG waveform. The waveforms of the infrared light signal are detected concurrently with the waveforms of the infrared light signal. The method includes calculating an average of products of the first similarity measures and the second similarity measures to estimate an adequacy of the red light signal and the infrared light signal.

In some embodiments, the reference PPG waveform is obtained based on a PPG measured from a fingertip. In some embodiments, the similarity measure is determined using the following formula $$\langle \vec{w}, \vec{f} \rangle = \max\left(0, \frac{\sum_{i=1}^{N} w_i f_i}{\sqrt{\sum_{i=1}^{N} w_i^2} \sqrt{\sum_{i=1}^{N} f_i^2}}\right),$$

wherein $\vec{w}$ is data representing the waveform of the red light signal or the waveform of the infrared light signal, and $\vec{f}$ is data representing the reference PPG waveform.

According to another example embodiment of the present disclosure, the steps of the method for performing pulse oximetry are stored on a non-transitory machine-readable medium comprising instructions, which when implemented by one or more processors perform the recited steps.

Other example embodiments of the disclosure and aspects will become apparent from the following description taken in conjunction with the following drawings.

BRIEF DESCRIPTION OF THE DRAWINGS

Embodiments are illustrated by way of example and not limitation in the figures of the accompanying drawings, in which like references indicate similar elements.

FIG. 3A is a block diagram illustrating transmission pulse oximetry.

FIG. 3B is a block diagram illustrating reflectance pulse oximetry.

DETAILED DESCRIPTION

Figure 1:
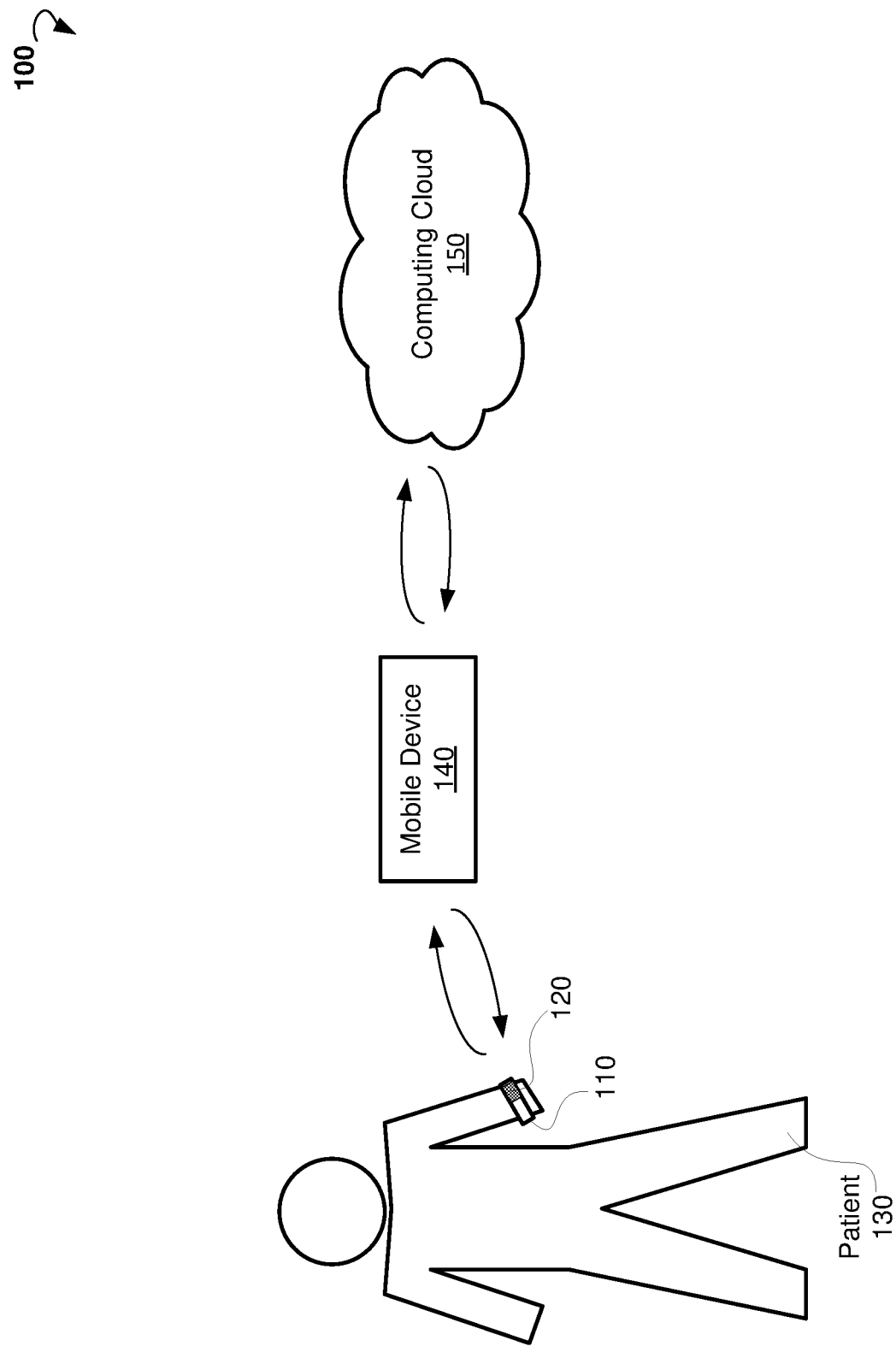
FIG. 1 is a block diagram showing an example system for performing pulse oximetry using a wearable device.

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical and electrical changes can be made without departing from the scope of what is claimed. The following detailed description is, therefore, not to be taken in a limiting sense, and the scope is defined by the appended claims and their equivalents.

The present disclosure provides systems and methods for performing pulse oximetry. Embodiments of the present disclosure can allow measuring medical parameters, for example, a PPG of a patient in a non-intrusive manner while, for example, the patient is at home, at work, outdoors, traveling, or is located at some other stationary or mobile environment. Some embodiments of the present disclosure include a wearable device. The wearable device can be worn at a wrist, ankle, chest, neck, or positioned at other sites of a human body. The wearable device can allow measuring the PPG of the patient without requiring the patient to take an active role in the process. The PPG data collected by the pulse oximetry during an extended period of time can be analyzed to detect and track trends in medical parameters, for example, oxygen saturation, and to make conclusions concerning symptoms and the progression of one or more chronic diseases from which the patient may suffer.

Embodiments of the present disclosure may facilitate measurements of $SpO_2$ oxygen saturation in blood in a pulsating artery using a reflectance pulse oximetry. The present techniques may be used to exclude an additive component in PPG signals due to reflection from skin and other non-pulsatile tissue covering the pulsating artery. The technology described herein may allow for estimating adequacy of the PPG signals taken during reflectance pulse oximetry.

According to some example embodiments, a method for performing pulse oximetry includes receiving at least three light signals reflected from a human tissue. The human tissue includes a pulsatile tissue and a non-pulsatile tissue. The three light signals are associated with at least three different wavelengths. The method allows determining, based on the three light signals, values of at least three functions. The three functions are invariant to oxygen saturation in the pulsatile tissue. The method includes determining, based on the values on the three functions, a first non-pulsatile component and a second non-pulsatile component. The method includes removing the first non-pulsatile component from an intensity of a red light signal reflected from the human tissue to estimate a first corrected intensity. The method includes removing the second non-pulsatile component from an intensity of an infrared light signal reflected from the human tissue to estimate a second corrected intensity. The method also includes calculating, based on the first corrected intensity and the second corrected intensity, a ratio of a red light absorption coefficient and an infrared light absorption coefficient. The method allows determining, based partially on the ratio of the first absorption coefficient and the second absorption coefficient, at least the oxygen saturation in the pulsatile tissue.

Referring now to FIG. 1, an example system 100 for performing pulse oximetry is shown. The system 100 can include at least a wearable device 110. The wearable device 110 can include sensors 120. In some embodiments, the wearable device 110 is worn by a patient 130 (for example, on a wrist, ankle, earlobe, neck, chest, fingertip, and the like) for an extended period of time. In various embodiments, the wearable device 110 can be carried out as a watch, a bracelet, a wristband, a belt, a neck band, and the like.

The wearable device 110 can be operable to constantly collect, via sensors 120, sensor data from a patient 130. Based on the sensor data, the wearable device 110 can be operable to generate PPG data, and, based on the PPG data, obtain further medical parameters, for example, oxygen saturation, pulse rate, and so forth.

In some embodiments, the system 100 includes a mobile device 140. The mobile device 140 can be communicatively coupled to the wearable device 110. In various embodiments, the mobile device 140 is operable to communicate with the wearable device 110 via a wireless connection such as, for example, Wi-Fi, Bluetooth™, Infrared (IR), and the like. The mobile device 140 can include a mobile phone, a smart phone, a phablet, a tablet computer, a notebook, and so forth. The mobile device 140 can be operable to receive the sensor data and analyze the sensor data to generate PPG data.

In further embodiments, the system 100 may include a cloud-based computing resource 150 (also referred to as a computing cloud). In some embodiments, the cloud-based computing resource 150 includes one or more server farms/clusters comprising a collection of computer servers and is co-located with network switches and/or routers. In certain embodiments, the mobile device 140 is communicatively coupled to the computing cloud 150. The mobile device 140 can be operable to send the sensor data to the computing cloud 150 for further analysis (for example, for extracting medical parameters from the sensor data and storing the results). The computing cloud 150 can be operable to run one or more applications and to provide reports regarding the health status of the patient, based on trends in medical parameters over time.

Figure 2:
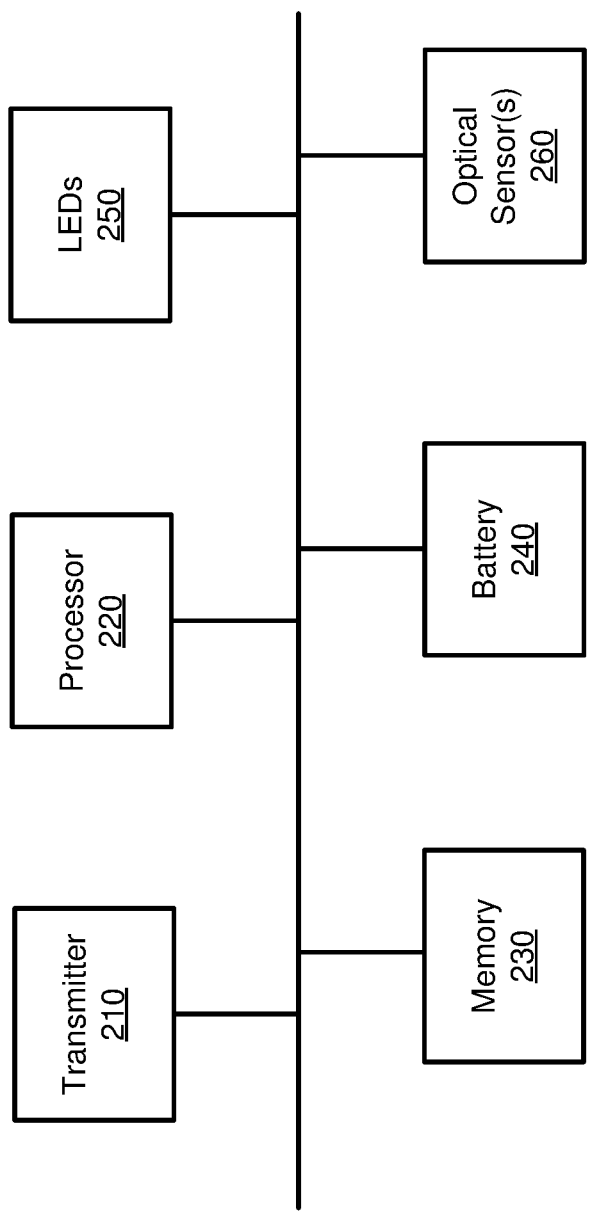
FIG. 2 is a block diagram showing components of an example device for performing pulse oximetry.

FIG. 2 is a block diagram illustrating components of wearable device 110, according to an example embodiment. The example wearable device 110 includes a transmitter 210, a processor 220, memory 230, a battery 240, at least two LEDs 250, and one or more optical sensor(s) 260. The wearable device 110 may comprise additional or different components to provide a particular operation or functionality. Similarly, in other embodiments, the wearable device 110 includes fewer components that perform similar or equivalent functions to those depicted in FIG. 2.

The transmitter 210 can be configured to communicate with a network such as the Internet, a Wide Area Network (WAN), a Local Area Network (LAN), a cellular network, and so forth, to send data streams (for example sensor data, PPG data, and messages).

The processor 220 can include hardware and/or software, which is operable to execute computer programs stored in memory 230. The processor 220 can use floating point operations, complex operations, and other operations, including processing and analyzing sensor data.

In some embodiments, the battery 240 is operable to provide electrical power for operation of other components of the wearable device 110. In some embodiments, the battery 240 is a rechargeable battery. In certain embodiments, the battery 240 is recharged using an inductive charging technology.

In various embodiments, the LEDs 250 are operable to emit light signals of a red wavelength (typically 660 nm) and infrared wavelength (660 nm). Each of the LEDs is activated separately and accompanied by a "dark" period where neither of the LEDs is on to obtain ambient light levels. In some embodiments, a single LED can be used to emit both the infrared and red light signals. The lights can be absorbed by human blood (mostly by hemoglobin). The methods for pulse oximetry are based on the fact that oxygenated hemoglobin absorbs more infrared light while deoxygenated hemoglobin absorbs more red light. Oxygenated hemoglobin allows more red light to pass through while deoxygenated hemoglobin allows more infrared light to pass through. The optical sensor(s) 260 (typically a photodiode) can receive light signals modulated by a human tissue. Based on the changes in the intensities of the modulated light signals, one or more medical parameters, such as, for example, oxygen saturation, arterial blood flow, pulse rate, and respiration, can be determined.

In some embodiments of the present disclosure, the LEDs 250 are also operable to emit light signals of isosbestic wavelengths (typically 810 nm and 520 nm). Both oxygenated hemoglobin and deoxygenated hemoglobin absorb the light of the isosbestic wavelengths equally.

The LEDs 250 and optical sensor(s) 260 can be utilized in either a transmission or a reflectance mode for pulse oximetry. In the transmission mode, the LEDs 250 and optical sensor(s) 260 are typically attached or clipped to a translucent body part (e.g., a finger, toe, and earlobe). The LEDs 250 are located on one side of the body part while the optical sensor(s) 260 are located directly on the opposite site. The light passes through the entirety of the body part, from one side to the other, and is thus modulated by the pulsating arterial blood flow. In the reflectance mode, the LEDs 250 and optical sensor(s) 260 are located on the same side of the body part (e.g. a forehead, finger, and wrist), and the light is reflected from the skin and underlying near-surface tissues back to the optical sensor(s) 260.

FIG. 3A is a block diagram illustrating details of transmission pulse oximetry. The light signal 310 emitted by LEDs 250 in red and infrared wavelengths are transmitted through pulsatile tissue 320 (for example, blood vessels in a highly perfused tissue such as a fingertip or an earlobe). The light signals 340 modulated across the pulsatile tissue 320 can be detected by optical sensor(s) 260. Some portions of the light signals 310 are reflected by non-pulsatile tissue 330 to produce a reflected light signal 350.

FIG. 3B is a block diagram illustrating details of reflectance pulse oximetry. Unlike the transmission pulse oximetry, light signal 310 emitted by LEDs 250 is reflected back to the optical sensor(s) 260 from both pulsatile tissue 320 (pulsating arteries) and non-pulsatile tissue 330 (e.g., skin and underlying tissue). In FIG. 3B, the corresponding reflected light signals are denoted as reflected light signal 360 and reflected light signal 350. The reflected light signal 350 from non-pulsatile tissue 330 has a negligible significance in conventional transmission oximetry (see FIG. 3A), as well as in strong signal reflectance oximetry when, for example, operated on a highly perfused tissue such as a fingertip or a forehead.

In case of a weak pulsatile signal, the non-pulsatile tissue reflection should be accounted for in order to avoid an erroneous $SpO_2$ reading. Therefore, the contribution of the non-pulsatile tissue needs to be identified and accounted for, to enable an accurate $SpO_2$ reading in such cases. The contribution of the non-pulsatile tissue depends on at least location of the optical sensor(s) 260 on the human tissue and a pressure of the optical sensor(s) 260 on the human tissue.

Figure 4:
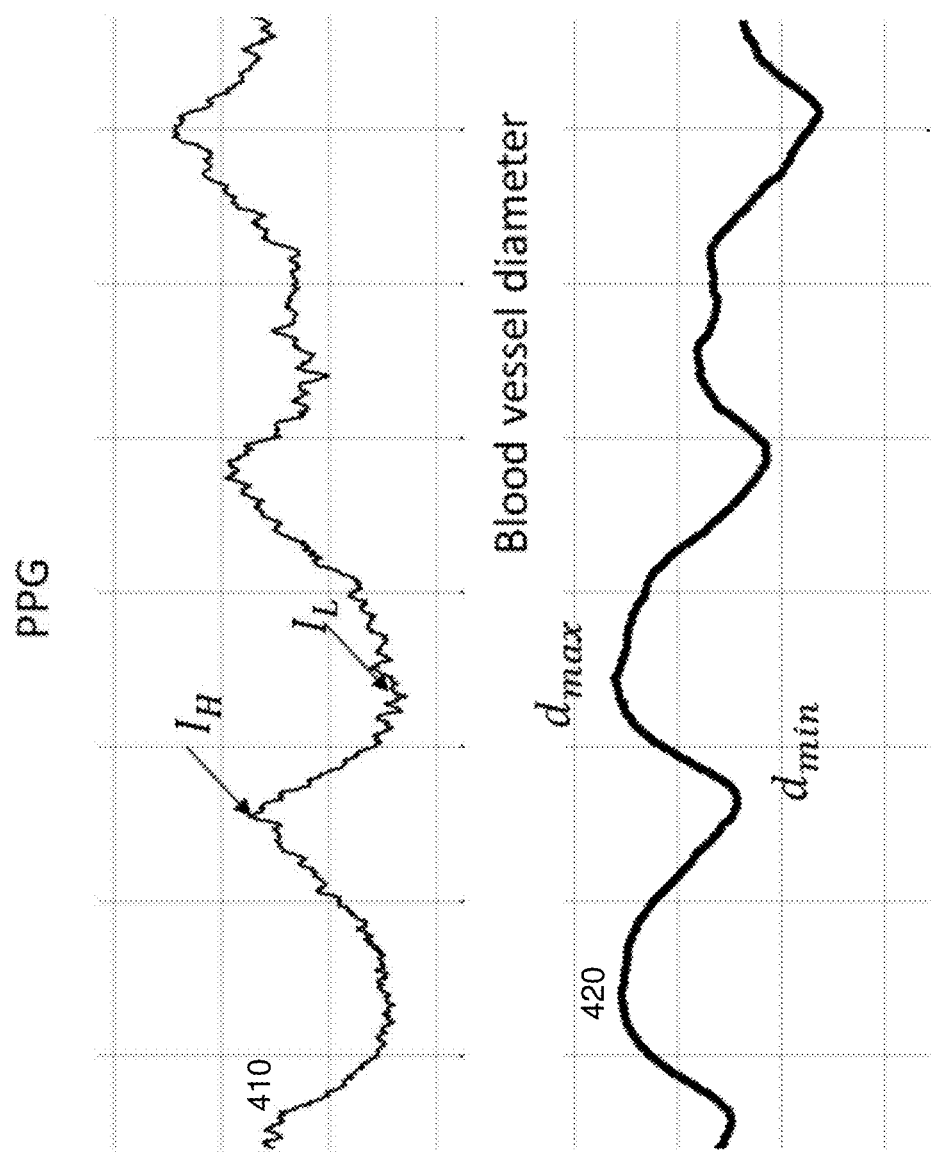
FIG. 4 shows an example plot of a PPG and example plot of a blood vessel diameter.

FIG. 4 shows a plot of example PPG 410 which can be obtained with reflectance pulse oximetry and a plot of blood vessel diameter 420. The PPG 410 represents the intensity I of a reflected light signal (either the red light signal or the infrared light signal) as modulated by a human tissue mostly due to a blood flow in the blood vessel. The high peaks (maximums) $I_H$ of PPG 410 correspond to the low peaks $d_{min}$ of the blood vessel diameter 420 and the low peaks $I_L$ of the PPG 410 correspond to the high peaks $d_{max}$ of the blood vessel diameter 420. The PPG 410 includes a component due to the reflection of a light from the non-pulsatile tissue (for example, skin).

Mapping of Measurement Conditions

In some embodiments, the detected signal I (the intensity of reflected light signal) is modeled as follows:

$$I = I_0(K_1 + K_2 e^{-cd}) \quad (1)$$

In formula (1), $I_0$ represents an incident light intensity, $K_1$ is a reflection coefficient of the non-pulsatile tissue (for example, a skin), $K_2$ indicates the absorption by pulsatile tissue, d represents (arterial) blood vessel diameter, and c is overall absorption coefficient of blood hemoglobin derived from a mixture of both oxygen-saturated and non-oxygen saturated hemoglobin. Each of oxygen-saturated and non-oxygen saturated hemoglobin has its own particular value of absorption coefficient c for a particular wavelength of emitted light signal 310.

In the transmission oximetry, $K_1$ is small relative to $K_2$ and therefore is neglected in both red light measurements and infrared light measurements. In the reflectance pulse oximetry or in the low perfusion transmission oximetry, the reflection coefficient $K_1$ cannot be neglected since the detected signal I is weak in such cases.

As shown in FIG. 4, the blood vessel diameter 420 changes periodically with the rhythm of the heart rate. The low peaks of the blood vessel diameter $d_{min}$ correspond to minimums of the absorption of the light by the blood and the high peaks of the light intensity $I_H$. The high peaks of the blood vessel diameter $d_{max}$ correspond to maximum absorption of the light by blood and the lowest peaks of the light intensity $I_L$. In some embodiments, the low peaks of the blood vessel diameter $d_{min}$ can be considered to be constant as they reflect lowest diastole. The high peaks of the blood vessel diameter $d_{max}$ may vary relatively slowly due to, for example, fluctuations of blood pressure.

The $SpO_2$ oxygen saturation can be calculated based on the ratio R of hemoglobin absorbance's coefficients measured at the red and infrared wavelengths. In general, for any two different wavelengths k and l, the ratio R can be defined as:

$$R_{k,l} = \frac{c_k}{c_l} \quad (2)$$

The relationship between the ratio $R_{red,ir}$ and the $SpO_2$ oxygen saturation is a non-linear, monotonically decreasing function. The relation between the ratio $R_{red,ir}$ may be described by an empirical curve function $f(R)$:

$$S = f(R_{red,ir}) \quad (3)$$

According to an example embodiment, the ratio $R_{k,l}$ may be calculated by the following process. In some embodiments, V≥0 denotes an arbitrary scalar representing the additive reflection component of the light from non-pulsatile tissue. A new term P is defined as:

$$P(I-V) = \log\left(\frac{I_H - V}{I_L - V}\right) \quad (4)$$

A linear approximation of (4) can be obtained for $I_H - I_L \ll I_L - V$:

$$P(I - V) = \log\left(1 + \frac{I_H - I_L}{I_L - V}\right) \approx \frac{I_H - I_L}{I_L - V} = \frac{AC}{DC - V} \quad (5)$$

Using Eq. 1, it can be shown that $$P(I - I_0 K_1) = \log\left(\frac{I_H - I_0 K_1}{I_L - I_0 K_1}\right) = \log\left(\frac{I_0 K_2 e^{-cd_{min}}}{I_0 K_2 e^{-cd_{max}}}\right) = c(d_{max} - d_{min}) \quad (6)$$

For any combination of two wavelengths, the ratio $R_{k,l}$ can be calculated as follows:

$$R_{k,l} = \frac{P(I_k - I_0^k K_1^k)}{P(I_l - I_0^l K_1^l)} \approx \frac{AC_k(DC_l - I_0^l K_1^l)}{(DC_k - I_0^k K_1^k)AC_l} \quad (7)$$

Figure 5:
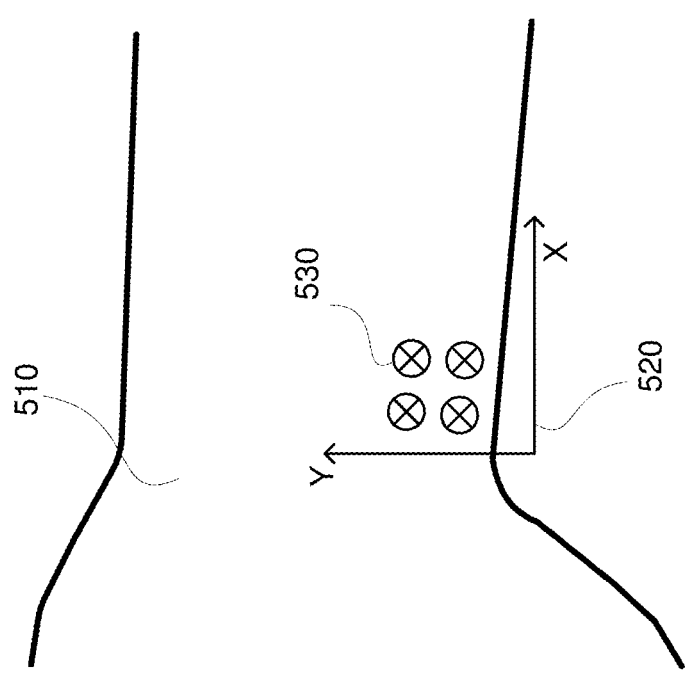
FIG. 5 shows location of a sensor and pressure of the sensor during $SpO_2$ measurements.

The correct calculation of $SpO_2$ oxygen saturation depends on accurate estimation of the additive reflection component V for the different wavelengths. The additive reflection component V also depends on physical conditions at which the pulse oximetry measurement are carried out. As illustrated in FIG. 5, the physical conditions include at least a particular location (for example, given by coordinates 520 x and y) of the optical sensor(s) 260 on the human tissue, for example, the wrist 510 and pressure 530 p with which the optical sensor(s) 260 is pressed to the human tissue.

For example, when a patient removes the wearable device 110 from a wrist and then replaces it, optical sensor(s) 260 is not placed at the same location. The location of the optical sensor(s) 260 can be changed slightly, for example within 0.5 centimeter. Additive reflection component V is changed when the optical sensor(s) 260 is replaced since reflected light comes through a different portion of non-pulsatile tissue. Therefore, a different additive reflection component V needs to be subtracted in Eq. (5).

In some embodiments, the light intensity for a particular wavelength is described as follows:

$$I(\vec{r}, S, d) = I_0(K_1(\vec{r}) + K_2(\vec{r})e^{-c(S)d}) \quad (8)$$

wherein vector $\vec{r}$ denotes the current physical conditions (x, y, p). Some embodiments assume that there is an invariant function G of the reflected signals with different wavelengths. The invariant function G is used to model the effect of the additive reflections from non-pulsatile tissue:

$$G(I_1, \ldots, I_l) = G(\vec{r}) \quad (9)$$

The function $G(I_1, \ldots, I_l)$ is an invariant on $SpO_2$ oxygen saturation S and the blood vessel diameter d. The invariant function G depends on physical condition (x, y, p), that is a location of the sensor and pressure of the sensor on skin. If the value of the invariant function G changes after the wearable device 110 is taken off a wrist and then is placed back, it may indicate that physical conditions (x, y, p) are changed.

Some embodiments assume that there is a pre-determined number of independent invariants of $SpO_2$ oxygen saturation. The physical conditions of a current pulse oximetry measurement can be reconstructed by values of invariant functions. Mapping the physical conditions to respective additive reflections V may allow correcting a calculation of $SpO_2$ oxygen saturation for the current physical conditions.

According to some example embodiments, the high peaks (maximums) of light intensity $I_H$ are used as an invariant function for each wavelength of the light:

$$I_H = I_0(K_1(\vec{r}) + K_2(\vec{r})e^{-c(S)d_{min}}) \quad (10)$$

The high peaks $I_H$ depend on vector ($\vec{r}$, S). The dependence on $SpO_2$ oxygen saturation S is minimal due to the relatively small amount of light absorbed during low diameter diastole and therefore $I_H$ can be considered approximately invariant to S. For example, if vector $\vec{r}$ is three dimensional vector (x, y, p), wherein (x, y) is a location of the sensor and p is the pressure of the sensor on skin, then using $I_H$ values for intensity of lights of three wavelengths can be used to build a proper mapping for the physical conditions.

In some embodiments, the high peaks of the light intensity $I_H$ at isosbestic wavelengths are used as the invariants on $SpO_2$ oxygen saturation S and blood vessel diameter d since the light absorption at the isosbestic wavelengths is independent of $SpO_2$ oxygen saturation since when a light of an isosbestic wavelength is used, the reflection from the oxygenized blood is the same as reflection from the non-oxygenized blood. In some embodiments, the isosbestic wavelengths include a near infrared wavelength 810 nm (NIR) and a green wavelength 520 nm (green). The corresponding highest peaks for the light intensities $I_H^{NIR}$ and $I_H^{green}$ can be considered as exact invariants on $SpO_2$ oxygen saturation.

In some embodiments, at the first usage of a wearable device 110, the patient 130 is instructed to wear and remove the wearable device a few times. Each time the wearable device 110 is put on, the patient 130 intentionally slightly changes sensor location and pressure of the sensor. During each time the user puts on the wearable device and wears it for a while, different physical conditions of $SpO_2$ oxygen saturation are mapped to values to one or more invariant functions. For example, values of invariant functions $I_H^{ir}$, $I_H^{red}$, and $I_H^{NIR}$ can be determined for the different physical conditions. Mapping is completed until no new information (no new values of the invariant functions) is received. Due to the restricted degrees of freedom allowed by the wearable device, the mapping process is expected to conclude quickly. Once mapping is complete, the physical condition may be reconstructed by calculating the values of the three invariant functions during regular operations.

During regular operations of the wearable device 110, each time the patient 130 puts the wearable device 110 on the wrist, values for invariant functions are determined, and based on the values of the invariant functions, proper values of additive reflection components for both an infrared light signal and red light signal is determined. In some embodiments, the additive refection components can be found via an empirically derived look up table. The proper value of additive refection components is then subtracted from peaks of PPG signals obtained with red and infrared lights to determine a correct ratio between hemoglobin absorbance coefficients at the red and infrared wavelengths. The ratio is then used to obtain a correct value of $SpO_2$ oxygen saturation.

Taking pulse oximetry measurements at a wrist requires high quality PPG signals to obtain a stable result. For optimal performance, the optical sensor(s) 260 should be placed directly on top of a pulsating artery such as the radial artery. An accurate placement of a wearable device on a wrist is difficult to control. In some embodiments, a morphological signal fit criterion is used to ensure PPG data adequacy. The fit criterion uses the morphology of the optical PPG signal measured from a finger as a benchmark.

The blood vessel diameter changes with the periodic rhythm of the heart rate. The changes of the blood vessel diameter influence the pulsatile component of the reflectance signal, while the non-pulsatile additive reflection depends on the location of the sensor with respect to the pulsating artery and on the pressure of the sensor pressed to the skin.

Signal Fit Criterion

The high peaks $I_H$ depend on vector ($\bar{r}$, S). The dependence on $SpO_2$ oxygen saturation S is minimal due to the relatively small amount of light absorbed during low diameter diastole and therefore $I_H$ can be considered approximately invariant to S. For example, if vector $\bar{r}$ is three dimensional vector (x, y, p), wherein (x, y) is a location of the sensor and p is the pressure of the sensor on skin, then using $I_H$ values for intensity of lights of three wavelengths can be used to build a proper mapping for the physical conditions.

In some embodiments, the high peaks of the light intensity $I_H$ at isosbestic wavelengths are used as the invariants on $SpO_2$ oxygen saturation S and blood vessel diameter d since the light absorption at the isosbestic wavelengths is independent of $SpO_2$ oxygen saturation since when a light of an isosbestic wavelength is used, the reflection from the oxygenized blood is the same as reflection from the non-oxygenized blood. In some embodiments, the isosbestic wavelengths include a near infrared wavelength 810 nm (NIR) and a green wavelength 520 nm (green). The corresponding highest peaks for the light intensities $I_H^{NIR}$ and $I_H^{green}$ can be considered as exact invariants on $SpO_2$ oxygen saturation.

In some embodiments, at the first usage of a wearable device 110, the patient 130 is instructed to wear and remove the wearable device a few times. Each time the wearable device 110 is put on, the patient 130 intentionally slightly changes sensor location and pressure of the sensor. During each time the user puts on the wearable device and wears it for a while, different physical conditions of $SpO_2$ oxygen saturation are mapped to values to one or more invariant functions. For example, values of invariant functions $I_H^{ir}$, $I_H^{red}$, and $I_H^{NIR}$ can be determined for the different physical conditions. Mapping is completed until no new information (no new values of the invariant functions) is received. Due to the restricted degrees of freedom allowed by the wearable device, the mapping process is expected to conclude quickly. Once mapping is complete, the physical condition may be reconstructed by calculating the values of the three invariant functions during regular operations.

During regular operations of the wearable device 110, each time the patient 130 puts the wearable device 110 on the wrist, values for invariant functions are determined, and based on the values of the invariant functions, proper values of additive reflection components for both an infrared light signal and red light signal is determined. In some embodiments, the additive refection components can be found via an empirically derived look up table. The proper value of additive refection components is then subtracted from peaks of PPG signals obtained with red and infrared lights to determine a correct ratio between hemoglobin absorbance coefficients at the red and infrared wavelengths. The ratio is then used to obtain a correct value of $SpO_2$ oxygen saturation.

Taking pulse oximetry measurements at a wrist requires high quality PPG signals to obtain a stable result. For optimal performance, the optical sensor(s) 260 should be placed directly on top of a pulsating artery such as the radial artery. An accurate placement of a wearable device on a wrist is difficult to control. In some embodiments, a morphological signal fit criterion is used to ensure PPG data adequacy. The fit criterion uses the morphology of the optical PPG signal measured from a finger as a benchmark.

The blood vessel diameter changes with the periodic rhythm of the heart rate. The changes of the blood vessel diameter influence the pulsatile component of the reflectance signal, while the non-pulsatile additive reflection depends on the location of the sensor with respect to the pulsating artery and on the pressure of the sensor pressed to the skin.

The additive reflection in PPG measurements from a finger is negligible, which makes the measurement of PPG from a finger a benchmark for signal adequacy. Empirically, the waveform of PPG obtained at the wrist approaches the typical waveform of PPG at the finger when the sensor is placed directly on top of and sufficiently tight to the pulsating artery.

In some embodiments, a similarity between a waveform of PPG taken from a wrist and a standard waveform of PPG taken from a fingertip is determined to estimate an adequacy of the PPG taken from the wrist. In certain embodiments, a similarity measure between a wrist PPG waveform $\{w_i\}_{i=1}^N$ and fingertip PPG waveform $\{f_i\}_{i=1}^N$ is calculated by the following formula:

$$\langle \vec{w}, \vec{f} \rangle = \max\left(0, \frac{\sum_{i=1}^{N} w_i f_i}{\sqrt{\sum_{i=1}^{N} w_i^2} \sqrt{\sum_{i=1}^{N} f_i^2}}\right)$$

In some embodiments, a signal fit score is defined as multiplication of similarity measure values for PPG taken with red light and PPG taken with infrared light, averaged over time:

$$Q_{fit} = \frac{1}{N} \sum_{k=1}^{N} \langle \vec{w}_{red}^k, \vec{f}_{red} \rangle \times \langle \vec{w}_{ir}^k, \vec{f}_{ir} \rangle \times 100\%$$

Figure 6:
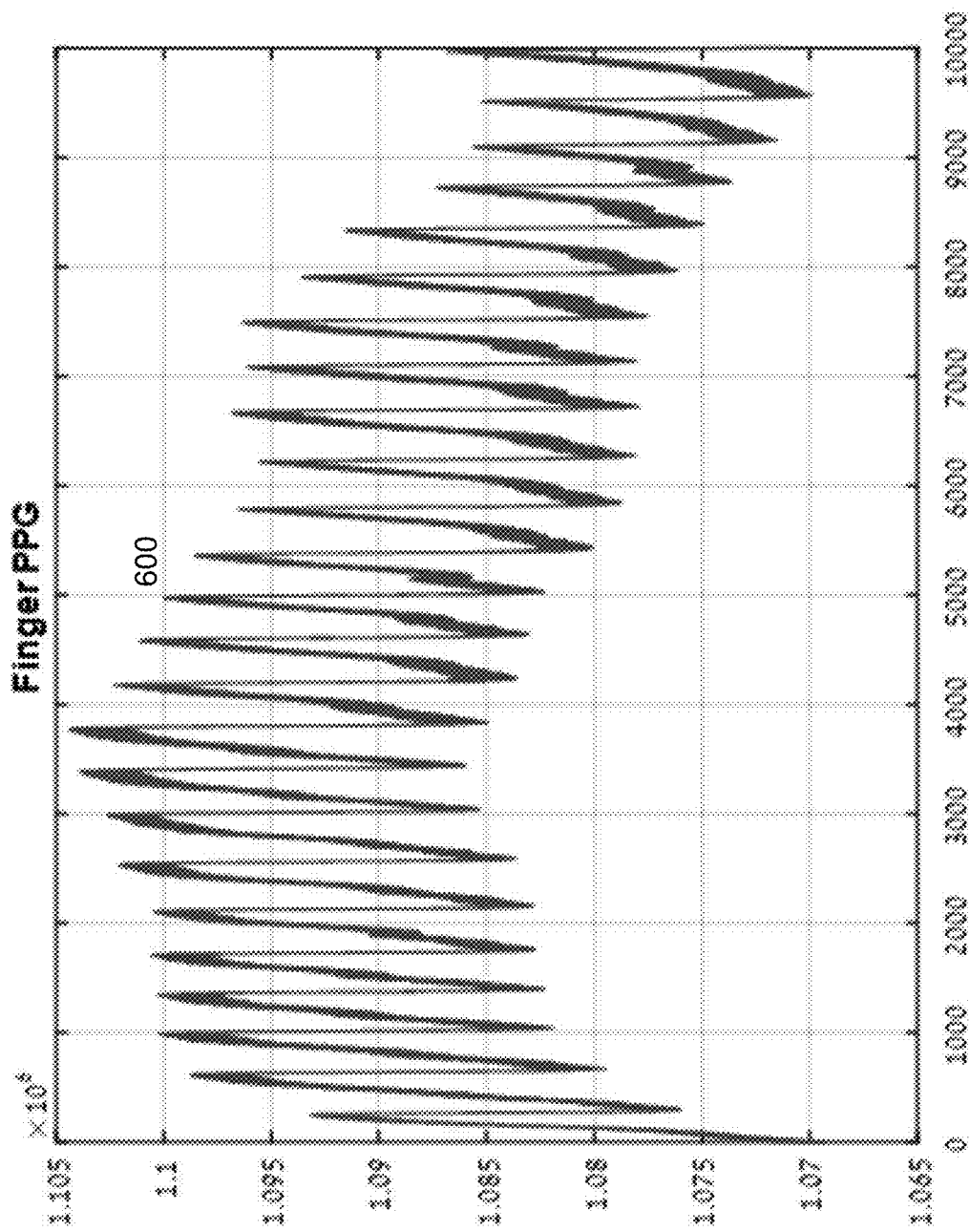
FIG. 6 illustrates an example plot of a PPG taken from a finger.

FIG. 6 illustrates example plot of a PPG 600 taken from a finger.

Figure 7:
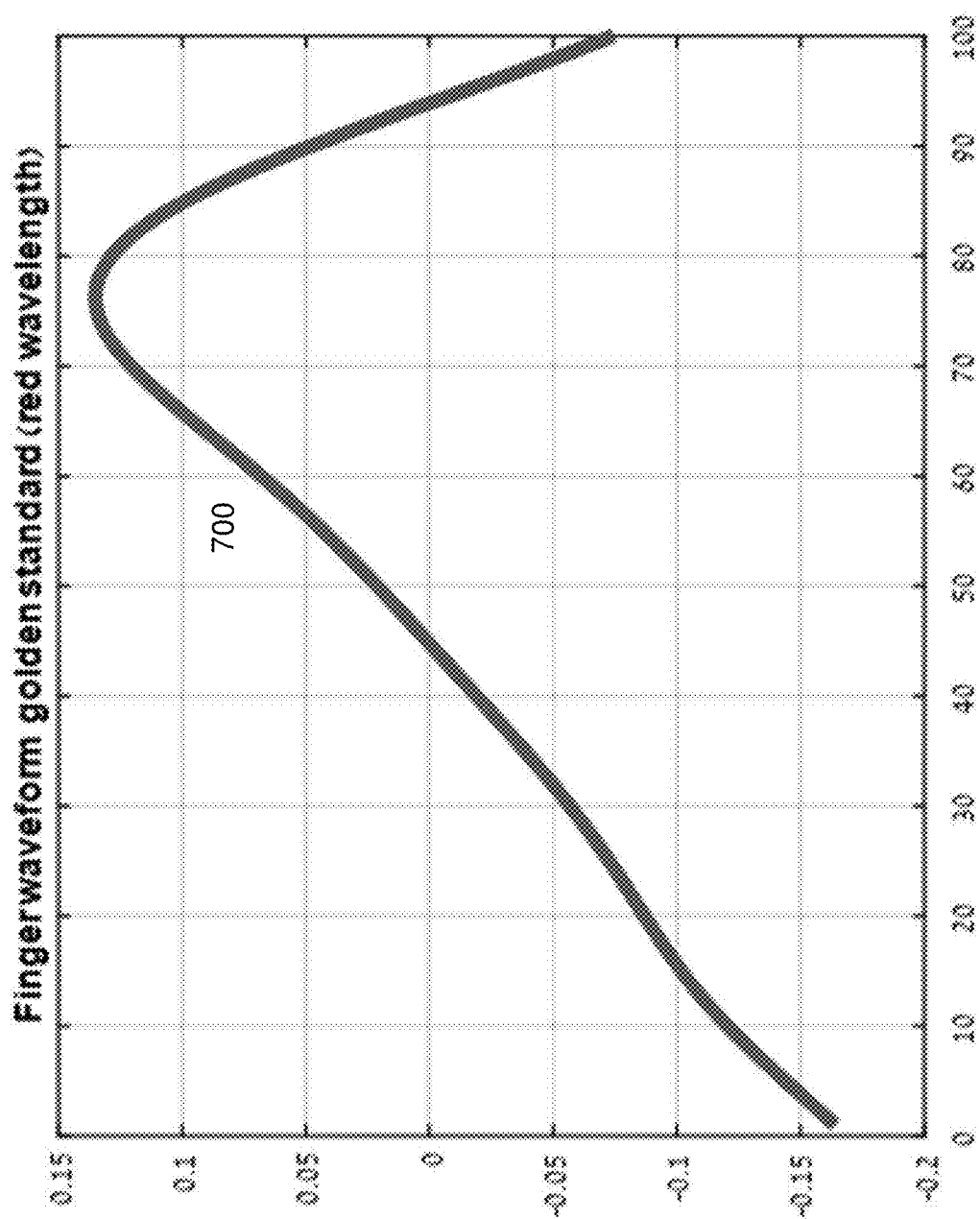
FIG. 7 illustrates example plots of a standard waveform of a PPG taken from a finger.

FIG. 7 illustrates example plots of a standard waveform 700 of a PPG taken from a finger. The standard waveform 700 is derived based on the PPG taken from a finger and can be used as standard waveform (a reference, a golden standard) for estimating adequacy of a PPG taken from a wrist.

Figure 8:
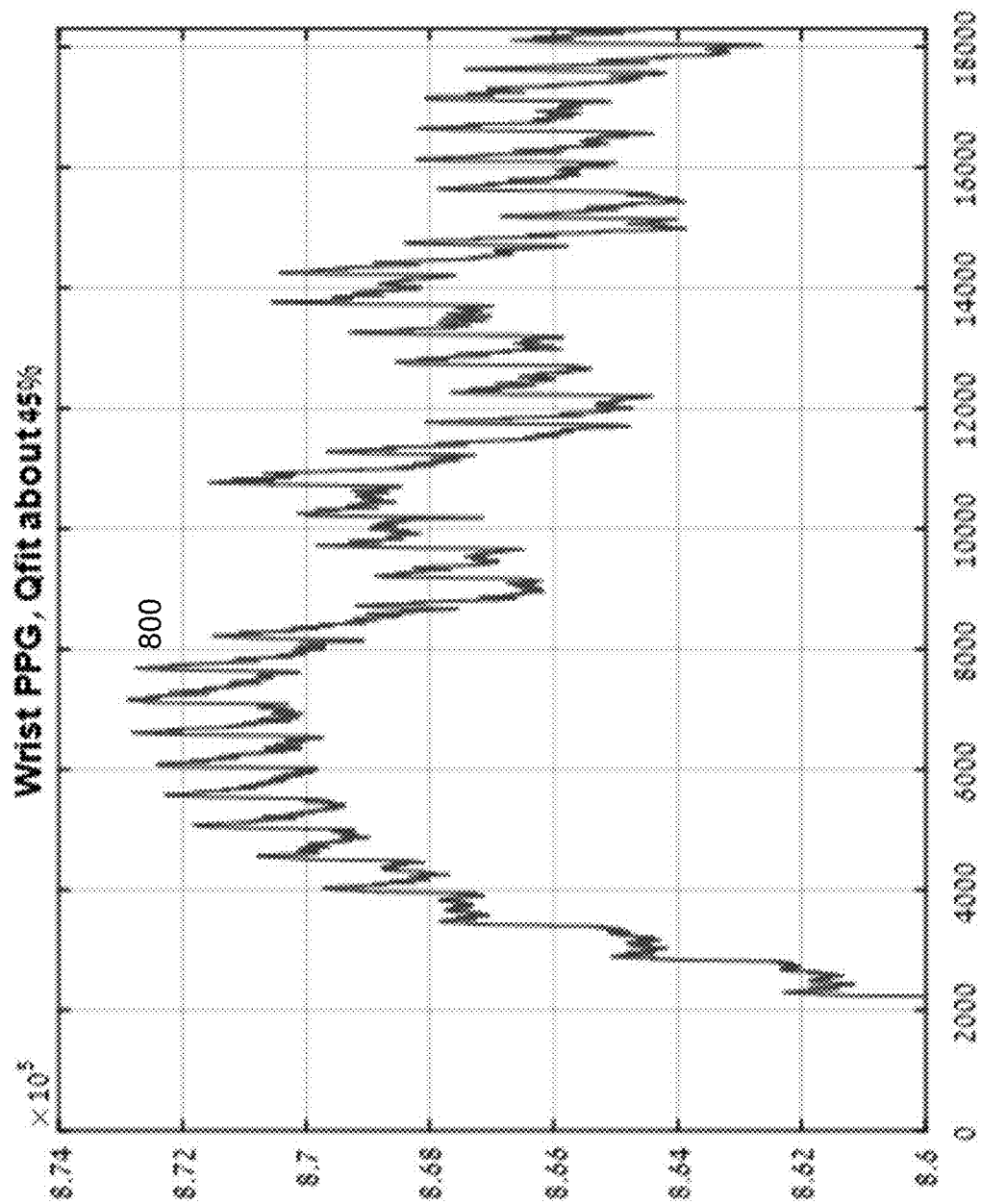
FIG. 8 illustrates an example plot of a PPG taken from a wrist.

FIG. 8 illustrates an example plot of a PPG taken from a finger. The waveforms of the PPG 800 are of markedly different morphology. The estimated adequacy of the PPG 800 is low since the signal fit score of PPG 800 is about 45%.

Figure 9:
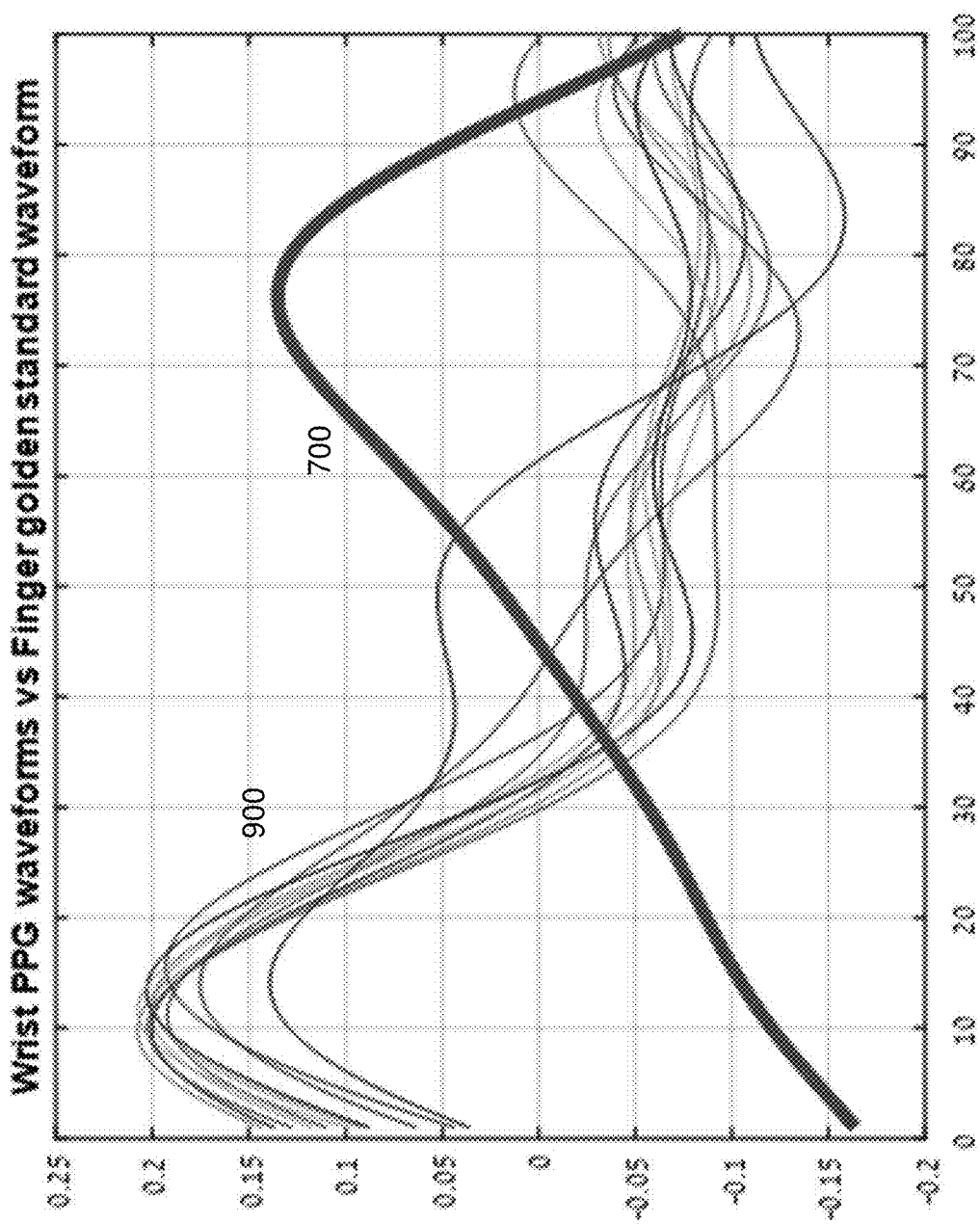
FIG. 9 illustrates an example plot of waveforms of PPGs taken from a wrist and a standard waveform of a PPG taken from a finger.

FIG. 9 illustrates an example plot waveforms 900 of PPGs taken from a wrist and the standard waveform 700 of a PPG taken from a finger.

Figure 10:
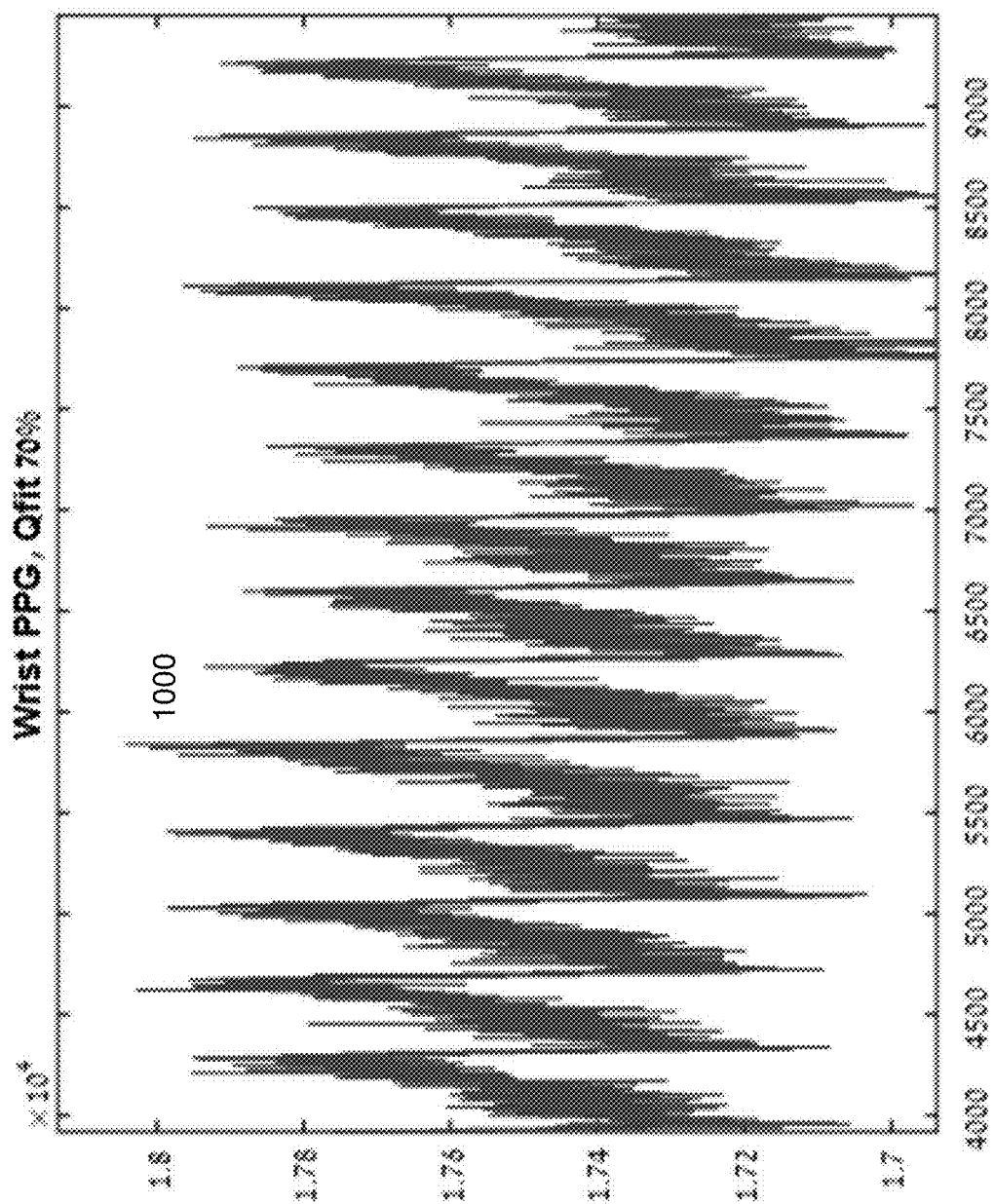
FIG. 10 illustrates another example plot of a PPG taken from a wrist.

FIG. 10 illustrates another example plot of a PPG 1000 taken from a wrist.

Figure 11:
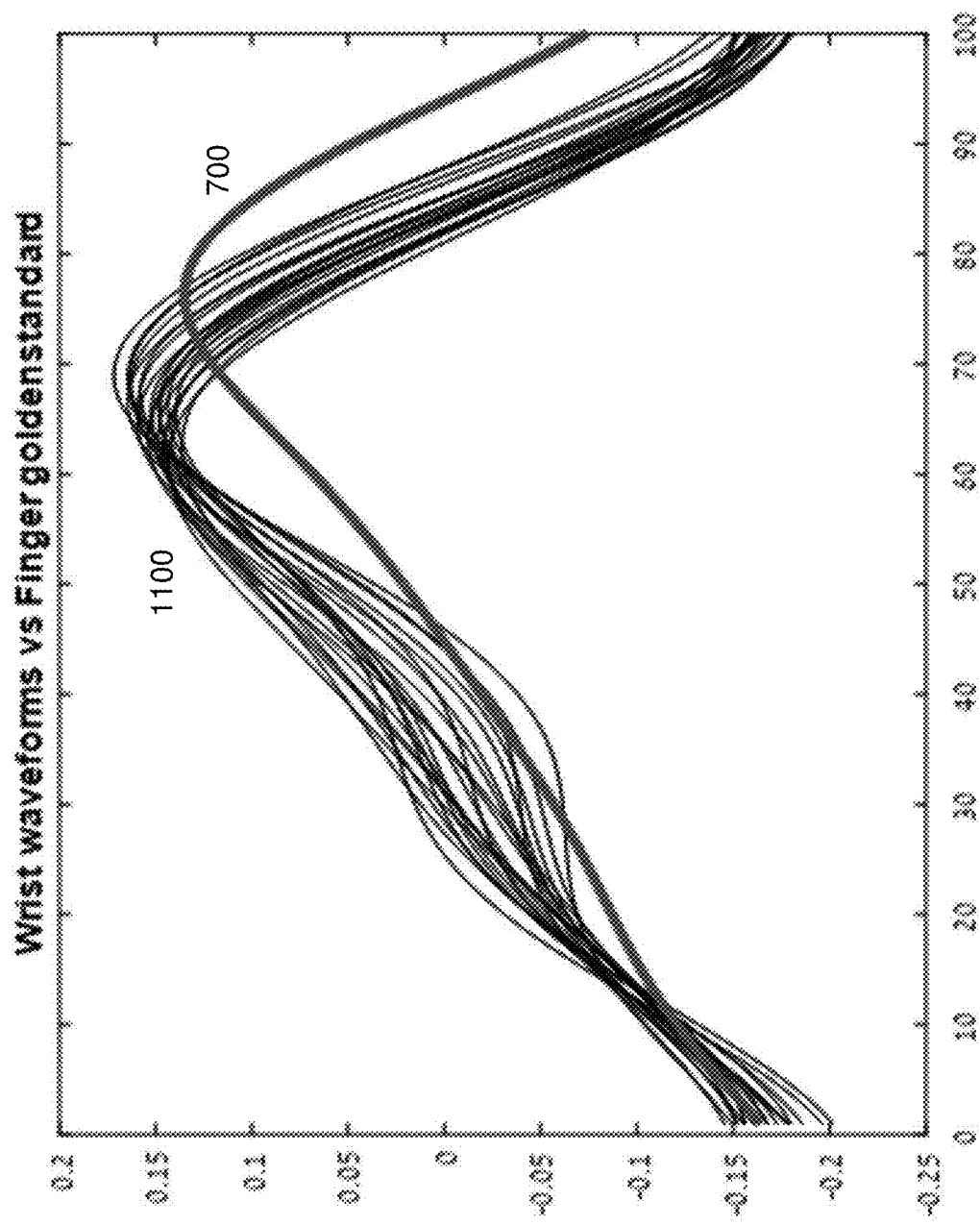
FIG. 11 illustrates an example plot of waveforms of PPGs taken from a wrist and a standard waveform of a PPG taken from a finger.

FIG. 11 illustrates an example plot of waveforms 1100 of PPG 1000 taken from a wrist and a standard waveform 700 of a PPG taken from a finger. The PPG 1000 is morphologically similar to a PPG taken from a wrist. The signal fit score of PPG 1000 is about 70%.

Figure 12:
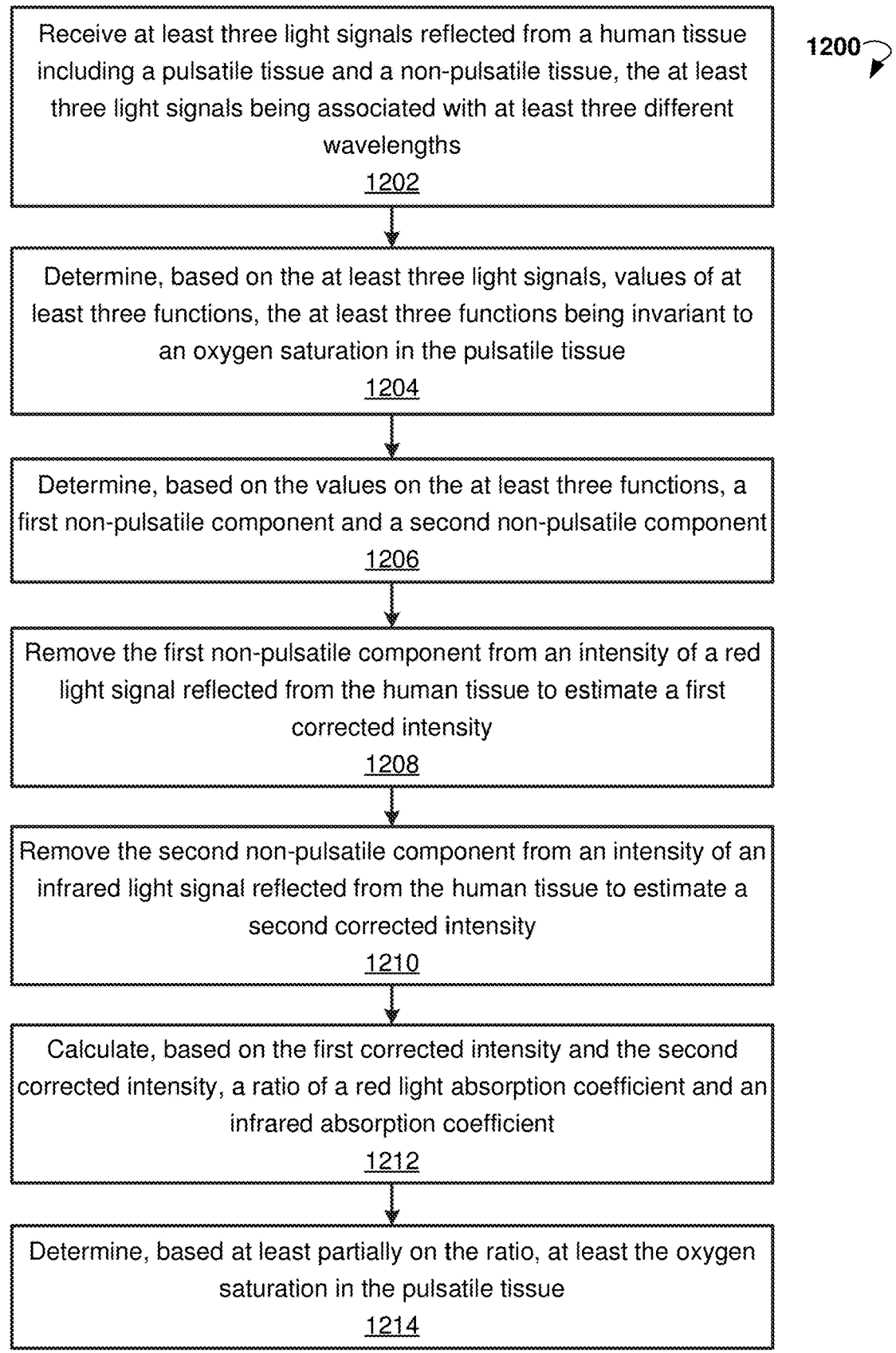
FIG. 12 is a flow chart showing an example method for performing pulse oximetry.

FIG. 12 is a flow chart showing steps of a method 1200 for performing pulse oximetry, according to an example embodiment. The method 1200 can be implemented using system 100 for performing pulse oximetry and a wearable device 110. Method 1200 can commence in block 1202 with receiving at least three light signals reflected from a human tissue. The human tissue includes a pulsatile tissue (for example, an artery) and a non-pulsatile tissue (for example, skin). The three light signals are associated with at least three different wavelengths. In some embodiments, the three light signals include a red light signal, an infrared light signal, and an isosbestic light signal.

In block 1204, the method 1200 proceeds with determining, based on the three light signals, values of at least three functions. The three functions are invariant to an oxygen saturation in the pulsatile tissue. In some embodiments, the three functions are the maximums of the intensities of the three light signals.

In block 1206, the method 1200 can determine, based on the values on the at least three functions, a first non-pulsatile component and a second non-pulsatile component. In some embodiments, the determination can be based on an empirically-derived lookup table.

In block 1208, the method 1200 can facilitate removing the first non-pulsatile component from an intensity of a red light signal reflected from the human tissue to estimate a first corrected intensity.

In block 1210, the method 1200 can facilitate removing the second non-pulsatile component from an intensity of an infrared light signal reflected from the human tissue to estimate a second corrected intensity.

In block 1212, the method 1200 proceeds with calculating, based on the first corrected intensity and the second corrected intensity, a ratio of a red light absorption coefficient and an infrared absorption coefficient.

In block 1214, the method 1200 proceeds with determining, based at least partially on the ratio, at least the oxygen saturation in the pulsatile tissue.

Figure 13:
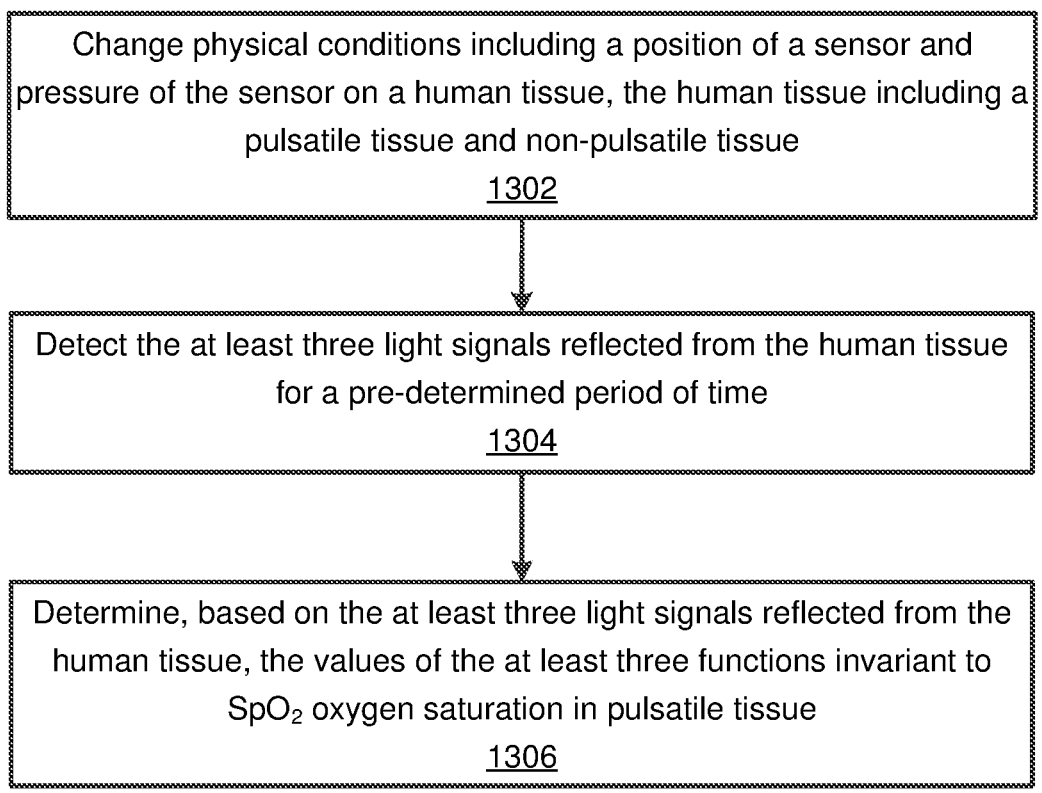
FIG. 13 is a flow chart showing an example method for mapping physical conditions of the pulse oximetry.

FIG. 13 is a flow chart showing steps of a method 1300 for mapping physical conditions of the pulse oximetry, according to an example embodiment. The method 1300 can be implemented using system 100 for performing pulse oximetry and a wearable device 110. Method 1300 can commence in block 1302 with changing physical conditions. The physical condition can include a location of a sensor on human tissue (for example at a wrist). The human tissue includes a pulsatile tissue (for example, a pulsating artery) and non-pulsatile tissue (for example, skin). In some embodiments, to change the physical conditions, patient 130 may be instructed to remove the wearable device 110 and place it back on a wrist at a slightly different place.

In block 1304, the method 1300 proceeds with detecting at least three light signals reflected from the human tissue for a predetermined period of time. The light signals are associated with three different wavelengths.

In block 1306, the method allows determining, based on the three light signals, the values of the at least three functions invariant to $SpO_2$ oxygen saturation in pulsatile tissue. In some embodiments, the three functions are the maximums of the intensities of reflection of the three lights from the human tissue. The steps of the method 1300 can be repeated several times until no new values of the three invariant functions are received.

Figure 14:
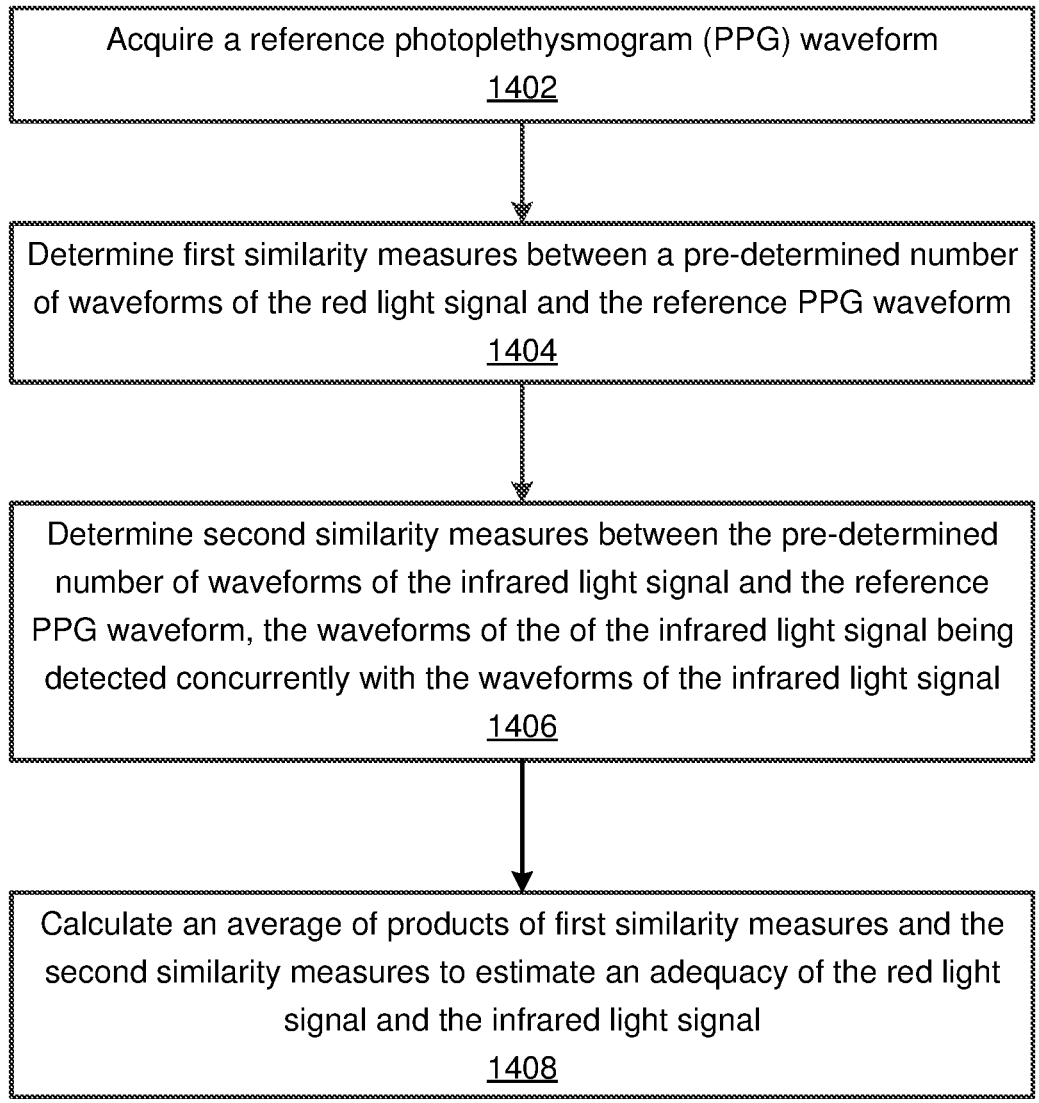
FIG. 14 is a flow chart showing an example method for estimating the adequacy of PPG data.

FIG. 14 is a flow chart showing steps of a method 1400 for estimating adequacy of a PPG data during pulse oximetry. The method 1400 may be implemented by system 100 for performing pulse oximetry and the wearable device 110.

Method 1400 can commence in block 1402 with acquiring a reference PPG waveform. In some embodiments, the reference PPG waveform includes a standard PPG waveform received with pulse oximetry measurements at a fingertip.

In block 1404, the method 1400 proceeds with determining first similarity measures between a pre-determined number of waveforms of the red light signal and the reference PPG waveform.

In block 1406, the method 1400 proceeds with determining second similarity measures between the pre-determined number of waveforms of the infrared light signal and the reference PPG waveform. The waveforms of the infrared light signal are detected concurrently with the waveforms of the infrared light signal.

In block 1408, the method 1400 calculates an average of products of first similarity measures and the second similarity measures to estimate the adequacy of the red light signal and the infrared light signal.

Figure 15:
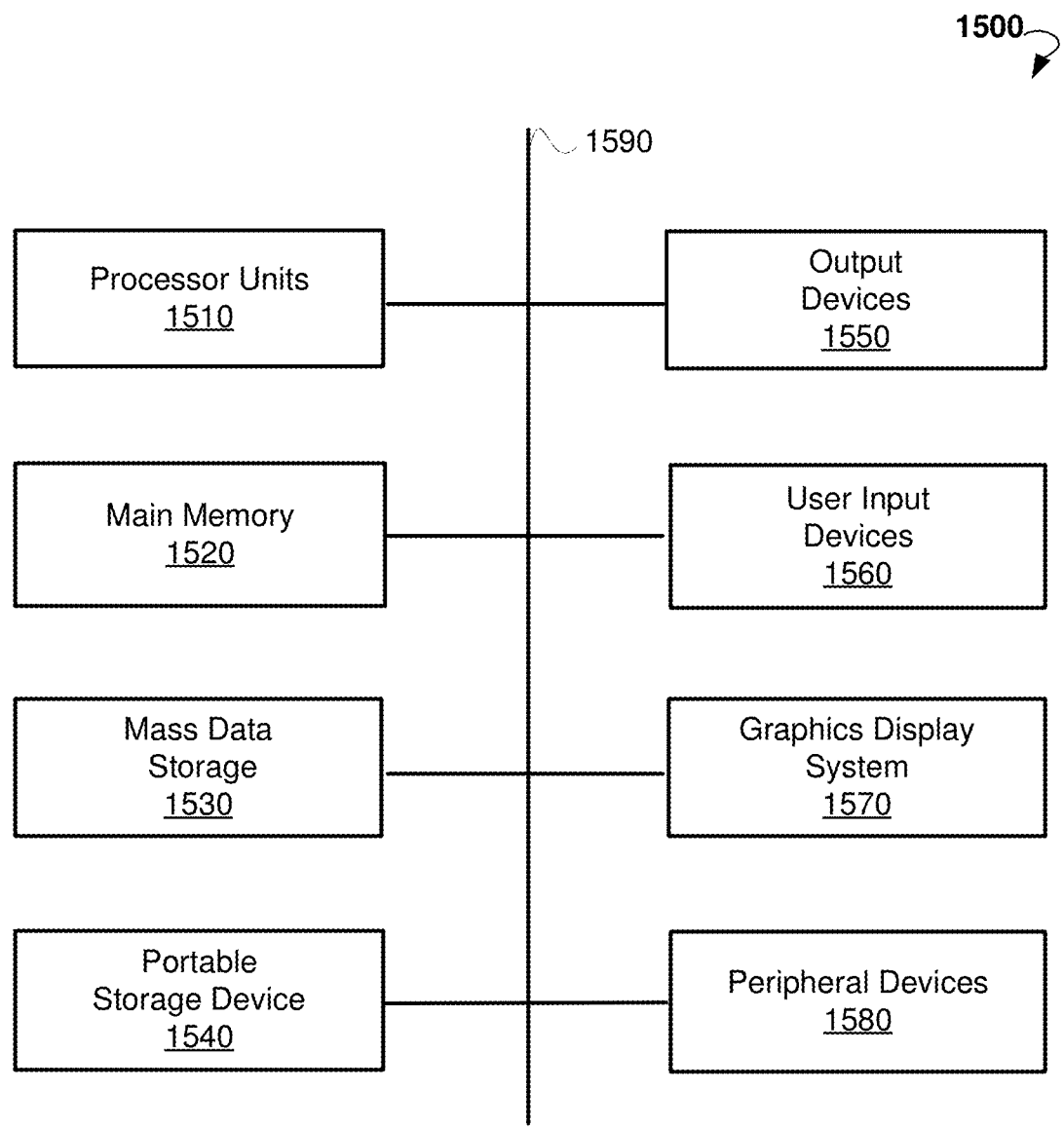
FIG. 15 shows a diagrammatic representation of a computing device for a machine, within which a set of instructions for causing the machine to perform any one or more of the methodologies discussed herein can be executed.

FIG. 15 illustrates a computer system 1500 that may be used to implement embodiments of the present disclosure, according to an example embodiment. The computer system 1500 may serve as a computing device for a machine, within which a set of instructions for causing the machine to perform any one or more of the methodologies discussed herein can be executed. The computer system 1500 can be implemented in the contexts of the likes of computing systems, networks, servers, or combinations thereof. The computer system 1500 includes one or more processor units 1510 and main memory 1520. Main memory 1520 stores, in part, instructions and data for execution by processor units 1510. Main memory 1520 stores the executable code when in operation. The computer system 1500 further includes a mass data storage 1530, a portable storage device 1540, output devices 1550, user input devices 1560, a graphics display system 1570, and peripheral devices 1580. The methods may be implemented in software that is cloud-based.

The components shown in FIG. 15 are depicted as being connected via a single bus 1590. The components may be connected through one or more data transport means. Processor units 1510 and main memory 1520 are connected via a local microprocessor bus, and mass data storage 1530, peripheral devices 1580, the portable storage device 1540, and graphics display system 1570 are connected via one or more I/O buses.

Mass data storage 1530, which can be implemented with a magnetic disk drive, solid state drive, or an optical disk drive, is a non-volatile storage device for storing data and instructions for use by processor units 1510. Mass data storage 1530 stores the system software for implementing embodiments of the present disclosure for purposes of loading that software into main memory 1520.

The portable storage device 1540 operates in conjunction with a portable non-volatile storage medium, such as a floppy disk, a compact disk, a Digital Versatile Disc (DVD), or USB storage device, to input and output data and code to and from the computer system 1500. The system software for implementing embodiments of the present disclosure is stored on such a portable medium and input to the computer system 1500 via the portable storage device 1540.

User input devices 1560 provide a portion of a user interface. User input devices 1560 include one or more microphones, an alphanumeric keypad, such as a keyboard, for inputting alphanumeric and other information, or a pointing device, such as a mouse, a trackball, stylus, or cursor direction keys. User input devices 1560 can also include a touchscreen. Additionally, the computer system 1500 includes output devices 1550. Suitable output devices include speakers, printers, network interfaces, and monitors.

Graphics display system 1570 includes a liquid crystal display or other suitable display device. Graphics display system 1570 receives textual and graphical information and processes the information for output to the display device. Peripheral devices 1580 may include any type of computer support device to add additional functionality to the computer system.

The components provided in the computer system 1500 of FIG. 15 are those typically found in computer systems that may be suitable for use with embodiments of the present disclosure and are intended to represent a broad category of such computer components that are well known in the art. Thus, the computer system 1500 can be a personal computer, handheld computing system, telephone, mobile computing system, workstation, tablet, phablet, mobile phone, server, minicomputer, mainframe computer, or any other computing system. The computer may also include different bus configurations, networked platforms, multi-processor platforms, and the like. Various operating systems may be used including UNIX, LINUX, WINDOWS, MAC OS, PALM OS, ANDROID, IOS, QNX, and other suitable operating systems.

It is noteworthy that any hardware platform suitable for performing the processing described herein is suitable for use with the embodiments provided herein. Computer-readable storage media refer to any medium or media that participate in providing instructions to a central processing unit, a processor, a microcontroller, or the like. Such media may take forms including, but not limited to, non-volatile and volatile media such as optical or magnetic disks and dynamic memory, respectively. Common forms of computer-readable storage media include a floppy disk, a flexible disk, a hard disk, magnetic tape, any other magnetic storage medium, a Compact Disk Read Only Memory disk, DVD, Blu-ray disc, any other optical storage medium, RAM, Programmable Read-Only Memory, Erasable Programmable Read-Only Memory, Electronically Erasable Programmable Read-Only Memory, flash memory, and/or any other memory chip, module, or cartridge.

In some embodiments, the computer system 1500 may be implemented as a cloud-based computing environment, such as a virtual machine operating within a computing cloud. In other embodiments, the computer system 1500 may itself include a cloud-based computing environment, where the functionalities of the computer system 1500 are executed in a distributed fashion. Thus, the computer system 1500, when configured as a computing cloud, may include pluralities of computing devices in various forms, as will be described in greater detail below.

In general, a cloud-based computing environment is a resource that typically combines the computational power of a large grouping of processors (such as within web servers) and/or that combines the storage capacity of a large grouping of computer memories or storage devices. Systems that provide cloud-based resources may be utilized exclusively by their owners or such systems may be accessible to outside users who deploy applications within the computing infrastructure to obtain the benefit of large computational or storage resources.

The cloud may be formed, for example, by a network of web servers that comprise a plurality of computing devices, such as the computer system 1500, with each server (or at least a plurality thereof) providing processor and/or storage resources. These servers may manage workloads provided by multiple users (e.g., cloud resource customers or other users). Typically, each user places workload demands upon the cloud that vary in real-time, sometimes dramatically. The nature and extent of these variations typically depends on the type of business associated with the user.

Thus, methods and systems for performing pulse oximetry have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A method for performing a pulse oximetry, the method comprising:
   receiving, by an optical sensor of a wearable device configured to be worn by a patient:
   a red light signal reflected from a human tissue of the patient, the human tissue including a pulsatile tissue and a non-pulsatile tissue, the red light signal being associated with a red wavelength;
   an infrared light signal reflected from the human tissue, the infrared light signal being associated with an infrared wavelength; and
   a third light signal reflected from the human tissue, the third light signal being associated with a third wavelength, the third wavelength being different from the red wavelength and the infrared wavelength;
   determining, by a processor communicatively coupled with the sensor and based on the red light signal, a first value of a first function invariant to an oxygen saturation in the pulsatile tissue;
   determining, by the processor and based on the infrared light signal, a second value of a second function invariant to the oxygen saturation in the pulsatile tissue;
   determining, by the processor and based on the third light signal, a third value of a third function invariant to the oxygen saturation in the pulsatile tissue;
   determining, by the processor, a first additive component in the red light signal and a second additive component in the infrared light signal, wherein the determining is based on the first value, the second value, and the third value, and wherein the first additive component and the second additive component are due to a reflection from the non-pulsatile tissue;
   removing, by the processor, the first additive component from an intensity of the red light signal to estimate a first corrected intensity;
   removing, by the processor, the second additive component from an intensity of the infrared light signal to estimate a second corrected intensity;
   calculating, by the processor and based on the first corrected intensity and the second corrected intensity, a ratio of a red light absorption coefficient and an infrared light absorption coefficient;
   determining, by the processor and based at least partially on the ratio, at least the oxygen saturation in the pulsatile tissue;
   acquiring, by the processor, a reference photoplethysmogram (PPG) waveform;
   determining, by the processor, first similarity measures between a pre-determined number of waveforms of the red light signal and the reference PPG waveform;

determining, by the processor, second similarity measures between a pre-determined number of waveforms of the infrared light signal and the reference PPG waveform, the waveforms of the infrared light signal being detected concurrently with the waveforms of the red light signal;

calculating, by the processor, an average of products Ai×Bi to estimate an adequacy of the red light signal and the infrared light signal, wherein Ai are the first similarity measures, Bi are the second similarity measures, and i=1, . . . , N, wherein N is the pre-determined number of waveforms of the red light signal;

estimating, by the processor, an estimate of the adequacy of the red light signal and the infrared light signal, based on the average of products;

collecting, by the processor and for a period of time, data concerning the red light signal, the infrared light signal, the third light signal, the adequacy, and the oxygen saturation;

analyzing, by the processor, the data to detect trends in the oxygen saturation; and providing, by the processor and based on the trends in the oxygen saturation, reports regarding a health status of the patient.

2. The method of claim 1, wherein the pulsatile tissue includes an artery and the non-pulsatile tissue includes skin.

3. The method of claim 1, wherein the human tissue includes one of the following: a fingertip, a wrist, an ankle, a neck, a chest, and an earlobe.

4. The method of claim 1, wherein the third light signal includes an isosbestic light signal, the isosbestic light signal including one of a near infrared light signal and a green light signal.

5. The method of claim 1, wherein the first value is a maximum of the intensity of the red light signal, the second value is a maximum of the intensity of the infrared light signal, and the third value is a maximum of an intensity of the third light signal.

6. The method of claim 1, wherein the first additive component and the second additive component are determined based on an empirically-derived lookup table.

7. The method of claim 1, further comprising mapping physical conditions, the physical conditions including a location of the optical sensor relative to the human tissue and a pressure of the optical sensor on the human tissue, to values of the first function, values of the second function, and values of the third function by repeatedly performing the following operations:

receiving, by the processor, an indication that the physical conditions are changed due to displacing the optical sensor relative to the human tissue;

detecting, by the optical sensor, the red light signal, the infrared light signal, and the third light signal for a predetermined period of time;

determining, by the processor and based on the red light signal, a value of the first function;

determining, by the processor and based on the infrared light signal, a value of the second function; and determining, by the processor and based on the third light signal, a value of the third function.

8. The method of claim 1, wherein the reference PPG waveform is obtained based on a PPG measured from a fingertip.

9. The method of claim 1, wherein at least one of the first similarity measures is determined using $$\langle \vec{w}, \vec{f} \rangle = \max\left(0, \frac{\sum_{i=1}^{N} w_i f_i}{\sqrt{\sum_{i=1}^{N} w_i^2} \sqrt{\sum_{i=1}^{N} f_i^2}}\right),$$

wherein $\vec{w}$ is data representing the waveform of the red light signal, and $\vec{f}$ is data representing the reference PPG waveform.

10. A system for performing a pulse oximetry, the system comprising:

at least one optical sensor of a wearable device, the wearable device being configured to be worn by a patient; and at least one processor communicatively coupled to the at least one optical sensor; and wherein:

the at least one optical sensor is configured to detect:
 a red light signal reflected from a human tissue of the patient, the human tissue including a pulsatile tissue and a non-pulsatile tissue, the red light signal being associated with a red wavelength;
 an infrared light signal reflected from the human tissue, the infrared light signal being associated with an infrared wavelength; and
 a third light signal reflected from the human tissue, the third light signal being associated with a third wavelength, the third wavelength being different from the red wavelength and the infrared wavelength; and the at least one processor is configured to:
 determine, based on the red light signal, a first value of a first function invariant to an oxygen saturation in the pulsatile tissue;
 determine, based on the infrared light signal, a second value of a second function invariant to the oxygen saturation in the pulsatile tissue;
 determine, based on the third light signal, a third value of a third function invariant to the oxygen saturation in the pulsatile tissue;
 determine a first additive component in the red light signal and a second additive component in the infrared light signal, wherein the determination is based on the first value, the second value, and the third value, and wherein the first additive component and the second additive component are due to reflection from the non-pulsatile tissue;
 remove the first additive component from an intensity of the red light signal to estimate a first corrected intensity;
 remove the second additive component from an intensity of the infrared light signal to estimate a second corrected intensity;
 calculate, based on the first corrected intensity and the second corrected intensity, a ratio of a red light absorption coefficient and an infrared light absorption coefficient;
 determine, based at least partially on the ratio, at least the oxygen saturation in the pulsatile tissue;
 acquire a reference photoplethysmogram (PPG) waveform;
 determine first similarity measures between a pre-determined number of waveforms of the red light signal and the reference PPG waveform;
 determine second similarity measures between a pre-determined number of waveforms of the infrared light signal and the reference PPG waveform, the waveforms of the infrared light signal being detected concurrently with the waveforms of the red light signal;

calculate an average of products Ai×Bi to estimate an adequacy of the red light signal and the infrared light signal, wherein Ai are the first similarity measures, Bi are the second similarity measures, and i=1, . . . , N, wherein N is a pre-determined number of waveforms of the red light signal;

estimate, by the processor, an estimate of the adequacy of the red light signal and the infrared light signal, based on the average of products;

collect, for a period of time, data concerning the red light signal, the infrared light signal, the third light signal, the adequacy, and the oxygen saturation;

analyze the data to detect trends in the oxygen saturation; and provide, based on the trends in the oxygen saturation, reports regarding a health status of the patient.

11. The system of claim 10, wherein the at least one optical sensor is configured to be placed on one of the following: a fingertip, a wrist, an ankle, a neck, a chest, and an earlobe.

12. The system of claim 10, wherein the third light signal includes an isosbestic light signal, wherein the isosbestic light signal includes one of a near infrared light signal and a green light signal.

13. The system of claim 10, wherein the first value is a maximum of the intensity of the red light signal, the second value is a maximum of the intensity of the infrared light signal, and the third value is a maximum of an intensity of the third light signal.

14. The system of claim 10, wherein the first additive component and the second additive component are determined based on an empirically-derived lookup table.

15. The system of claim 10, wherein the at least one processor is further operable to map physical conditions, the physical conditions including a location of the at least one optical sensor relative to the human tissue and a pressure of the at least one optical sensor on the human tissue, to values of the first function, values of the second function, and values of the third function by repeatedly performing the following operations:

receiving an indication that the physical conditions are changed due to displacing the at least one optical sensor relative to the human tissue;

receiving, via the at least one optical sensor, the red light signal, the infrared light signal, and the third light signal for a pre-determined period of time;

determining, based on the red light signal, a value of the first function;

determining, based on the third light signal, a value of the second function; and determine, based on the infrared light signal, a value of the third function.

16. The system of claim 10, wherein the at least one optical sensor is configured to be placed on a fingertip to measure a PPG, the reference PPG waveform being obtained based on the PPG.

17. The system of claim 10, wherein at least one of the similarity measures is determined using $$\langle \vec{w}, \vec{f} \rangle = \max\left(0, \frac{\sum_{i=1}^{N} w_i f_i}{\sqrt{\sum_{i=1}^{N} w_i^2} \sqrt{\sum_{i=1}^{N} f_i^2}}\right)$$

wherein $\vec{w}$ is data representing the waveform of the red light signal, and $\vec{f}$ is data representing the reference PPG waveform.

18. A non-transitory computer-readable storage medium having embodied thereon instructions, which when executed by a processor, perform steps of a method, the method comprising:

receiving:
a red light signal reflected from a human tissue of a patient, the human tissue including a pulsatile tissue and a non-pulsatile tissue, the red light signal being associated with a red wavelength;

an infrared light signal reflected from the human tissue, the infrared light signal being associated with an infrared wavelength; and a third light signal reflected from the human tissue, the third light signal being associated with a third wavelength, the third wavelength being different form the red wavelength and the infrared wavelength;

determining, based on the red light signal, a first value of a first function-invariant to an oxygen saturation in the pulsatile tissue;

determining, based on the infrared light signal, a second value of a second function invariant to the oxygen saturation in the pulsatile tissue;

determining, based on the third light signal, a third value of a third function invariant to the oxygen saturation in the pulsatile tissue;

determining a first additive component in the red light signal and a second additive component in the infrared light signal, wherein the determination is based on the first value, the second value, and the third value, and wherein the first additive component and the second additive component are due to reflection from the non-pulsatile tissue;

removing a first non-pulsatile component from an intensity of the red light signal to estimate a first corrected intensity;

removing a second non-pulsatile component from an intensity of the infrared light signal to estimate a second corrected intensity;

calculating, based on the first corrected intensity and the second corrected intensity, a ratio of a red light absorption coefficient and an infrared light absorption coefficient;

determining, based partially on the ratio, at least the oxygen saturation in the pulsatile tissue;

acquiring a reference photoplethysmogram (PPG) waveform;

determining first similarity measures between a pre-determined number of waveforms of the red light signal and the reference PPG waveform;

determining second similarity measures between a pre-determined number of waveforms of the infrared light signal and the reference PPG waveform, the waveforms of the infrared light signal being detected concurrently with the waveforms of the red light signal;

calculating an average of products Ai×Bi to estimate an adequacy of the red light signal and the infrared light signal, wherein Ai are the first similarity measures, Bi are the second similarity measures, and i=1, . . . , N, wherein N is the pre-determined number of waveforms of the red light signal;

estimating, by the processor, an estimate of the adequacy of the red light signal and the infrared light signal, based on the average of products;

collecting, for a period of time, data concerning the red light signal, the infrared light signal, the third light signal, the adequacy, and the oxygen saturation;
analyzing the data to detect trends in the oxygen saturation; and
providing, based on the trends in the oxygen saturation, reports regarding a health status of the patient.

\* \* \* \* \*